United States Patent [19]

Chu et al.

[11] Patent Number: 4,957,858

[45] Date of Patent: Sep. 18, 1990

[54] REPLICATIVE RNA REPORTER SYSTEMS

[75] Inventors: Barbara Chu, Del Mar, Calif.; Fred R. Kramer, New York, N.Y.; Paul Lizardi, Cuernavaca, Mexico; Leslie E. Orgel, La Jolla, Calif.

[73] Assignees: The Salk Instute for Biological Studies, San Diego, Calif.; The Trustees of Columbia University, New York, N.Y.

[21] Appl. No.: 852,692

[22] Filed: Apr. 16, 1988

[51] Int. Cl.[5] .......... C12Q 1/68

[52] U.S. Cl. .......... 435/6; 435/7; 435/91; 435/188; 436/501; 436/547; 536/27; 530/387; 935/78

[58] Field of Search .......... 435/6, 7, 91, 188, 810; 436/501, 547, 827; 536/27; 935/78; 530/387

[56] References Cited

U.S. PATENT DOCUMENTS

| | | | |
|---|---|---|---|
| 3,444,042 | 5/1969 | Spiegelman et al. . | |
| 3,444,044 | 5/1969 | Spiegelman . | |
| 3,661,893 | 5/1972 | Spiegelman et al. . | |
| 3,689,475 | 9/1972 | Spiegelman et al. . | |
| 4,228,237 | 10/1980 | Hevey et al. | 435/7 |
| 4,478,914 | 10/1984 | Giese | 428/407 |
| 4,542,104 | 9/1985 | Stryer et al. | 436/536 |
| 4,556,643 | 12/1985 | Paau et al. | 436/501 |
| 4,683,195 | 7/1987 | Mullis et al. | 435/6 |
| 4,683,202 | 7/1987 | Mullis | 435/91 |
| 4,711,955 | 12/1987 | Ward et al. | 536/29 |
| 4,749,647 | 6/1988 | Thomas et al. | 935/78 X |
| 4,786,600 | 11/1988 | Kramer et al. | 435/6 |

FOREIGN PATENT DOCUMENTS

| | | |
|---|---|---|
| 0097373 | 1/1984 | European Pat. Off. . |
| 0122614 | 10/1984 | European Pat. Off. . |
| 0135108 | 3/1985 | European Pat. Off. . |
| 0151492 | 8/1985 | European Pat. Off. . |
| 0154884 | 9/1985 | European Pat. Off. . |
| 8403285 | 8/1984 | PCT Int'l Appl. . |

OTHER PUBLICATIONS

Saiki et al., "Enzymatic Amplification of Beta-Globin Genomic Sequences and Restriction Site Analysis for Diagnosis of Sickle Cell Anemia," Science 230, 1350-1354 (1985).

Chu et al., "Synthesis of an Amplifiable Reporter RNA for Bioassays," Nucleic Acids Research 14, 5591-5603 (1986).

Chu and Orgel, "Detection of Specific DNA Sequences with Short Biotin-Labeled Probes," DNA 4, 327-331 (1985).

Murasugi et al., "Biotin-Labeled Oligonucleotides: Enzymatic Synthesis and Use as Hybridization Probes," DNA 3, 269-277 (1984).

Renz, "Polynucleotide-Histone Hl Complexes as Probes for Blot Hybridization," EMBO Jour. 2, 817-822 (1983).

Miele, et al., "Autocatalytic Replication of a Recombinant RNA," J. Mol. Biol. 171, 281-295 (1983).

Alagon et al., "Activation of Polysaccharides with 2-Iminothiolane and its Uses," Biochemistry 19, 4341-4345 (1980).

Benton et al., "Screening Lambda(gt) Recombinant Clones by Hybridization to Single Plaques in situ," Science 196 180-182 (1977).

Bresser et al., "Biological Activity of mRNA Immobilized on Nitrocellulose in NaI," Biochemistry 80 6523-6527 (1983).

Brigati et al., "Detection of Viral Genomes in Cultured Cells and Paraffin-Embedded Tissue Sections Using Biotin-labeled Hybridization Probes," Virology 126 32-50 (1983).

Britten and Kohne, "Repeated Sequences in DNA," Science 161 527-540 (1968).

Cosstick et al., "Fluorescent Labelling of tRNA and Oligodeoxynucloetides Using T4 RNA Ligase," Nucl. Acids Res. 12 1791-1810 (1984).

Donis-Keller, "Site-specific Enzymatic Cleavage of RNA," Nucl. Acids Res. 7 179-192 (1979).

Dreyer et al., "Sequence-specific Cleavage of Single-stranded DNA: Oligodeoxynucleotide-EDTA-Fe(II)," Proc. Natl. Acad. Sci. (U.S.A.) 82 968-972 (1985).

Foster et al., "Non-radioacive Hybridization Probes Prepared by the Chemical Labelling of DNA and RNA with a Novel Reagent, Photobiotin," Nucl. Acids Res. 13 745-761 (1985).

Gillespie et al., "A Quantitative Assay for DNA-RNA Hybrids with DNA Immobilized on a Membrane," J. Mol. Biol. 12 829-842 (1965).

Gordon et al., "The Surface Glycoproteins of Human Skin Fibroblasts Detected after Electrophoresis by the Binding of Peanut (*Arachis hypogae*) Agglutinin and Castor-Bean Agglutinin I," Biochem. J. 208 351-358 (1982).

Hand et al., "Definition of Antigenic Heterogeneity and Modulation among Human Mammary Carcinoma Cell Populations using Monoclonal Antibodies to Tumor-associated Antigens," Cancer Research 43 728-735 (1983).

(List continued on next page.)

*Primary Examiner*—Amelia Burgess Yarbrough
*Attorney, Agent, or Firm*—Fitch, Even, Tabin & Flannery

[57] ABSTRACT

Highly sensitive methods for assaying for biopolymers, such as by immunoassay or nucleic acid probe hybridization assay, and compositions for carrying out the methods, are provided. The methods employ as reporter group a RNA capable of being autocatalytically replicated by an RNA-dependent RNA polymerase, such as the replicase of bacteriophage Q$\beta$. The high sensitivity of the assay methods is due to the rapid, exponential increase in concentration of such a replicative RNA, associated specifically with biopolymer analyte, that can be achieved by autocatalytic RNA replication.

45 Claims, No Drawings

OTHER PUBLICATIONS

Haruna et al., "Autocatalytic Synthesis of a Viral RNA in vitro," Science 150 884–886 (1965).
Imam et al., "Generation and Immunohistological Characterization of Human Monoclonal Antibodies Carcinoma Cells," Cancer Res. 45 263–271 (1985).
Kacian et al., "A Replicating RNA Molecule Suitable for a Detailed Analyisis of Extracellular Evolution and Replication," Proc. Nat. Acad. Sci. (U.S.A.) 69 3038–3042 (1972).
Kafatos et al., "Determination of Nucleic Acid Sequence Homologies and Relative Concentation by a Dot Hybridization Procedure," Nuc. Acids Rec. 7 1541–1552 (1979).
Kaufman et al., "Covalent Joining of Phenylanine Transfer Ribonucleic Acid Half-Molecules by T4 RNA Ligase," Proc. Nat. Acad. Sci. (U.S.A.) 71 3741–3745 (1974).
Kohne et al., "Room Temperature Method for Increasing the Rate of DNA Reassociation by Many Thousandfold: The Phenol Emulsion Reassociation Technique," Biochemistry 16, 4329–5341 (1977).
Kössel et al., "The Terminal Addition of Riboadenylic Acid to Deoxyoligonucleotides by Terminal Deoxynucleotidyl Transferase as a Tool for the Specific Labelling of Deoxyoligonucleotides at the 3′-Ends," Eur. J. Biochem. 22. 271–276 (1971).
Langer et al., "Enzymatic Synthesis of Biotin-labeled Polynucleotides: Novel Nucleic Acid Affinity Probes," Proc. Natl. Acad. Sci. (U.S.A.) 78, 6633–6637 (1981).
Leary et al., "Rapid and Sensitive Colorimetic Method for Visualizing Biotin-Labeled DNA Probes Hybridized to DNA Immobilized on Nitrocellulose: Bio-blots," Proc. Natl. Acad. Sci. (U.S.A.) 80, 4045–4049 (1983).
Matthews et al., "Enchanced Chemiluminescent Method for the Detction of DNA Dot-Hybridization Assays," Analytical Biochem. 151, 205–209 (1985).
Oi et al., "Fluorescent Phycobiliprotein Conjugates for Analyses of Cells and Molecules," J. Cell Bio. 93 981–986 (1982).
Saris et al., "Blotting of RNA on to Ion Exchange Paper Allowing Subsequent Characterization by in situ Translation in Addition to Blot Hybridization," Nucl. Acids Res. 10 4831–4843 (1982).
Stellwag et al., "Electrophoretic Transfer of DNA, RNA and Protein onto Diazobenzyloxymethyl (DBM)-Paper," Nucl. Acids Res. 8 299–317 (1980).
Thomas, "Hybridization of Denatured RNA and Small DNA Fragments Transferred to Nitrocellulose," Proc. Natl. Acad. Sci. (U.S.A.) 77 5201–5205 (1980).
Uhlenbeck et al., "Equimolar Addition to Oligoribunucleotides with T4 RNA Ligase," Nucl. Acids Res. 4, 85–98 (1977).
White et al., "Cytoplasmic Dot Hybridization," J. Biol. Chem. 257, 8569–8572 (1982).
Kramer et al, "Evolution in vitro: Sequence and Phenotype of a Mutant RNA Resistant to Ethidium Bromide," J. Mol. Biol. 89, 719–736 (1974).
Igloi, "A Silver Stain for the Detection of Nanogram Amounts of tRNA Following Two-Dimensional Electrophoresis," Anal. Biochem. 134 184–188 (1983).
Kutateladze et al., "New Procedure of High-Voltage Electrophoresis in Polyacrylamide Gel and its Application to the Sequencing of Nucleic Acids," Anal. Biochem. 100, 129–135 (1979).
Sammons et al., "Ultrasensitive Silver-based Color Staining of Polypeptides in Polyacrylamide Gels," Electrophoresis 2, 135–141 (1981).
Sharp et al., "Detection of Two Restriction Endonuclease Activities in *Haemophilus parainfluenzae* Using Analytical Agarose-Ethidium Bromide Electrophoresis," Biochemistry 12, 3055–3063 (1973).
Miyake et al., "Grouping of RNA Phages Based on the Template Specificity of Their RNA Replicases," Proc. Natl. Acad. Sci. (U.S.A.) 68, 2022–2024 (1971).
Eoyang et al., "Q-Beta RNA Polymerase from Phage Q-Beta-Infected *E. coli*," Cantoni and Davies, eds., *Procedures in Nucleic Acid Research*, 3, 829–839 (1971).
Chu and Orgel, "Nonenzymatic Sequence-specific Cleavage of Single-Stranded DNA," Proc. Natl. Acad. Sci. (U.S.A.) 82, 963–967 (1985).
Lewin, R. Science 222 (1983): 1313–1315.

REPLICATIVE RNA REPORTER SYSTEMS

The United States Government has certain rights in the invention described and claimed herein as a result of support of work related to said invention under grants from the United States National Institutes of Health.

The present invention is directed to assays for biopolymers, including polynucleotides and polypeptides, and more particularly to such assays which employ reporter systems based on RNAs which are templates for self-replication catalyzed by RNA-dependent RNA polymerases.

BACKGROUND OF THE INVENTION

It is sometimes necessary to detect a small amount of a specific biopolymer in a sample which includes a background of a much larger quantity of unrelated material. Some important cases are immunoassays for viruses or anti-pathogen antibodies present at very low levels in blood or other body fluids of infected individuals or for proteins present at very low levels in cell lysates; assays for sparse receptors on cell surfaces; and nucleic acid probe hybridization assays for pathogenic bacteria present at very low levels in food, for pathogenic protozoan parasites, bacteria or viruses present at low levels in body fluids, or for short segments of defined sequence indicative of genetic abnormalities in the total genomic DNA of a species.

The specificity of such an assay depends on the use of an affinity molecule that binds specifically to a biopolymer analyte (i.e., a particular target biopolymer, or a particular target site or segment of a biopolymer) which is present in a sample only if the entity being tested for (e.g., virus, other microogranism, cells with particular receptors, abnormal gene) is present. Examples of affinity molecules include an antibody for a protein target, that is the antigen used to elicit the antibody; an oligonucleotide with a sequence complementary to that of a target segment of a target DNA or RNA; an antigen for an antibody target, which is an antibody elicited by the antigen; and a lectin which binds specifically to a particular carbohydrate moiety of a target glycoprotein or target polysaccharide.

Detection of an affinity molecule, which has bound to any of its biopolymer analyte that is present in a sample being assayed, is achieved typically by complexing with, or including in, the affinity molecule a reporter group which, as part of a reporter system, can produce a detectable signal. The sensitivity of an assay will depend on both the specificity of binding between the affinity molecule and the biopolymer analyte in assay systems, the specificity of the reporter system in providing signal only from affinity molecule in an assay system, and the intensity of signal generated by the reporter system in an assay system.

Typical reporter systems employ fluorescent organic moieties or $^{32}$P-labeled phosphate groups as reporter groups. The sensitivity that can be achieved with these types of reporter systems, which involve signal directly from reporter groups, is fundamentally limited by the number of reporter groups needed to produce a signal of detectable intensity. This number is about $10^6$. Thus, with these groups, no fewer than about $10^5$ target molecules, or target segments, can be detected in an assay.

The sensitivity of non-radioactive assays for biopolymer analytes has been improved by employing enzyme adducts linked to an affinity molecule. For example, an oligonucleotide or DNA affinity molecule "probe", that is biotinylated, is detected by complexing enzyme-linked avidin reporter group with the biotinyl groups and then detecting product from a reaction catalyzed by the enzyme. Langer et al., Proc. Natl. Acad. Sci. (U.S.A.) 78, 6633–6637 (1981); Leary et al., Proc. Natl. Acad. Sci. (U.S.A.) 80, 4045–4049 (1983). See also, with regard to enzyme-linked avidin as reporter group in immunoassays, Hevey and Malmros, U.S. Pat. No. 4,228,237. By joining an enzyme to the affinity molecule and then providing substrate for a reaction catalyzed by the enzyme, it is possible to accumulate a large number of product molecules for each enzyme-affinity molecule-analyte complex, and hence, in principle, obtain sensitivities much greater than is possible using small reporter molecules directly. Peroxidase and phosphatase, enzymes that are readily assayed by sensitive colorimetric methods, are widely used in enzyme-adduct reporter groups. Leary et al., supra.

However, enzyme-adduct reporter systems, such as that involving phosphatase linked to avidin, are fundamentally limited in sensitivity by the rates at which reactions catalyzed by the enzymes of a reporter group can occur. As a practical matter, a detectable quantity of a product of the enzyme-catalyzed reaction must be produced in an assay within some reasonable time period, between about 1 to about 100 hours. In practice, enzyme-adduct reporter systems are about 10 to 100 times less sensitive than reporter systems based on $^{32}$P-decay.

There exists a need for reporter systems that are more sensitive, even to the extent that the presence of a single molecule of target biopolymer or single target biopolymer segment can, in principle, be detected in an assay that takes no longer than a few hours. Such a reporter system requires that the presence of the analyte be detected through a reaction that produces a prodigious number of product molecules, per analyte molecule or segment, in a relatively short time.

An enzymatically catalyzed, nucleic acid polymerization reaction generates, from a template, a chain of complementary sequence, which is also a substrate for the involved polymerase. Thus, repeat reactions increase the numbers of particular nucleotide chains exponentially. Accordingly, there are advantages in utilizing the self-replicability of nucleic acids to provide sensitivity in reporter systems An example of the use of a nucleic acid polymerization reaction to render detectable a minute amount of analyte is provided by R. K. Saiki et al., Science 230, 1350–1354 (1985) and European Patent Application Publication No. 0 164 054. Saiki et al., supra, employ E. coli DNA polymerase I, together with dATP, dCTP, dGTP and dTTP and two synthetic oligonucleotide primers, one with a sequence complementary to a segment near the 3'-end of the sense strand and the other with a sequence complementary to a segment near the 3'-end of the anti-sense strand of the analyte DNA segment, to increase the quantity of analyte in a sample to a level that is readily detectable by standard DNA probe assay techniques. The Saiki et al. procedure involves a number of cycles of DNA polymerase-catalyzed replication, strand-separation, and primer annealing. The amount of analyte increases exponentially with the number of cycles, at least until the concentration of primed segments for replication exceeds the concentration of polymerase molecules. The procedure described in Saiki et al. requires at least three synthetic oligonucleotides, the two primers as well as at least one probe for detection of analyte. Each cycle of replication in the Saiki et al. procedure has three-steps. Thus, while the Saiki et al. procedure enhances sensitivity of a DNA probe assay by exploiting the self-replicability of DNA to increase the amount of analyte, there remains a need for simpler and more generally applicable procedures whereby the sensitivity of assays for biopolymers or particular segments thereof or sites thereon is enhanced through the self-replicability of nucleic acids.

Enzymatically catalyzed, RNA-directed, RNA polymerizations generate complementary chains rapidly and without need for primers. The numbers of RNA chains increase exponentially with repeated reaction cycles in RNA-directed, RNA polymerizations. Unlike other such polymerizations in vitro, the RNA-directed, RNA polymerizations proceed continuously without need for strand-separation and primer-annealing between cycles. Enzymatically catalyzed, RNA-directed, RNA polymerization has been termed "autocatalytic replication." Haruna and Spiegelman, Science 150, 884–886 (1965). Until the present invention, it has not been appreciated that autocatalytic replication can be employed to provide convenient, broadly applicable, highly sensitive reporter systems for biopolymer analytes.

Miele et al., J. Mol. Biol. 171, 281–295 (1983) describe the insertion of a decaadenylic acid segment into a mutant midivariant-1 RNA at a position which is not essential for function of the RNA-dependent RNA polymerase ("replicase") of bacteriophage Qβ and report that the recombinant midivariant-1 RNA remains active as a template for replication by the replicase. See also Kramer et al., U.S. patent application Ser. No. 614,350, filed May 25, 1984, which is incorporated herein by reference. The Kramer et al. application describes recombinant RNA templates, based on midivariant and similar RNAs, for replication by Qβ replicase activity and the use of such templates as nucleic acid hybridization probes. Neither the Miele et al. article nor the Kramer et al. patent application suggests the use of a replicative RNA and an associated RNA-dependent RNA polymerase as the basis of a reporter system for assays for biopolymer analytes. Further, neither the article nor the patent application suggests that a recombinant replicative RNA, used as a probe for a target nucleic acid segment, could be replicated subsequent to hybridization with target to increase the sensitivity of assays employing the probe.

SUMMARY OF THE INVENTION

The present invention is based on our discovery that the autocatalytic replication in vitro of certain RNAs can be employed to provide highly sensitive reporter systems for assays for biopolymer analytes.

Thus, the present invention relates to reporter systems for highly enhanced sensitivity in assays for detection of specific biopolymer analytes. The reporter systems are based upon the rapid and exponential, enzyaecatalyzed replication of RNAs capable of being replicated in vitro by an RNA-directed RNA polymerase, including midivariant-1 RNA and mutants thereof capable of being replicated in vitro by the RNA polymerase of bacteriophage Qβ.

The reporter systems of the invention involve joining such a replicative RNA to an affinity molecule, which binds specifically to a biopolymer analyte in an assay. If the analyte is a segment of a polynucleotide, the replicative RNA may be linked to a polynucleotide or oligonucleotide affinity molecule, which may be either a DNA or a RNA and which includes a segment, with a sequence complementary to that of the analyte segment, whereby hybridization can occur with the analyte segment. If the analyte is a protein, such as, for example, a coat protein of a virus or a protein of interest released upon lysis of cells in a culture, the RNA may be linked to an antibody affinity molecule which binds specifically with the analyte protein in an assay system. If the analyte is a molecule, such as a glycoprotein or a polysaccharide, which includes a carbohydrate moiety, the replicative RNA may be linked to a lectin affinity molecule which binds specifically to the carbohydrate moiety.

The replicative RNA can be joined to the affinity molecule before or after the affinity molecule has complexed with any of its biopolymer analyte present in an assay system.

Because, after replicative RNA is joined to an affinity molecule, replication of the RNA is required to render detectable affinity molecule that has bound to analyte, either (a) the RNA is joined to the affinity molecule in a manner that allows the RNA, while joined, to be replicated by a RNA-dependent RNA polymerase or (b) the RNA is joined to the affinity molecule in a manner that allows the RNA to be severed from the affinity molecule in a form whereby the severed RNA can be replicated by a RNA-dependent RNA polymerase.

The detection of the RNA replicated from the replicative RNA bound to affinity molecule, that in turn had bound to analyte in an assay system, is accomplished by any of numerous known techniques. For example, the replication of the RNA can be carried out with radioactively labeled ribonucleoside-5'-triphosphates, and detection is then of radioactive RNA resulting from the replication. Alternatively, a biotinylated ribonucleoside-5'-triphosphate can be employed as a substrate in the replication process and any resulting biotinylated RNA can be detected using an enzyme-avidin adduct as disclosed by, for example, Leary et al., supra. Also, replicated RNA can be detected directly by its ultraviolet absorbance or by staining.

DETAILED DESCRIPTION OF THE INVENTION

In one of its aspects, the present invention is a method of determining the presence of an analyte in a sample, which method comprises (i) exposing the sample to an affinity molecule for said analyte under conditions whereby binding occurs between the affinity molecule and the analyte;

(ii) if said affinity molecule is not itself a replicative RNA, joining, either before or after step (i), a replicative RNA to the affinity molecule employed in step (i);

(iii) employing a RNA-dependent RNA polymerase to catalyze replication of replicative RNA that is or had been joined to affinity molecule that bound to analyte or that is affinity molecule that had been bound to analyte; and (iv) detecting RNA made by the reaction of step (iii).

In another of its aspects, the invention entails an affinity molecule-replicative RNA hybrid molecule, i.e., and affinity molecule joined to a replicative RNA. The affinity molecule can be joined to the replicative RNA through a first linking moiety, covalently joined to the replicative RNA without eliminating the replicability of the replicative RNA by a RNA-dependent RNA polymerase, and a second linking moiety, joined to the affinity molecule without eliminating the specificity of binding between affinity molecule and its analyte, said first and second linking moieties being covalently joined to each other, being a specific binding pair, or forming simultaneously, with a common third linking moiety, specific binding pairs.

The invention also entails "smart probes," which are compounds in which an affinity molecule, which is a nucleic acid, is covalently joined to a replicative RNA and in which the affinity molecule portion is associated with the replicative RNA portion so that the replicative RNA is inactive as a template for replication by an RNA-dependent RNA polymerase unless the affinity molecule is associated with analyte of affinity molecule.

The invention entails further an affinity molecule non-covalently joined to a replicative RNA through base-pairing.

In yet a further aspect, the invention involves a replicative RNA joined to a linking moiety, without eliminating the replicability of the replicative RNA by an RNA-dependent RNA polymerase, said linking moiety being one of a pair of linking moieties whereby linkage between the replicative RNA and an affinity molecule, joined to the other linking moiety of the pair, can be effected by covalent joining of the linking moieties or by interaction of the linking moieties as a specific binding pair.

Such a replicative RNA joined, in accordance with the invention, to one of a pair of linking moieties, is a universal reporter group for any affinity molecule joined, in a manner that does not eliminate the specificity of its binding to its analyte, to the other linking moiety of the pair.

"Analyte" means a substance whose presence, concentration or amount in a sample is being determined in an assay. An analyte is sometimes referred to as a target substance or a target segment of an assay. With assays according to the present invention, the analyte is usually a biopolymer or a segment of a biopolymer. Analytes include, for example, proteins, including glycoproteins and lipoproteins, enzymes, hormones, receptors, antigens, and antibodies; nucleic acids (DNAs and RNAs); segments of nucleic acids; and polysaccharides.

With assays of the present invention, an analyte is often associated with a biological entity which is present in a sample if and only if the analyte is present. Such biological entities include viroids (analyte is the nucleic acid or a segment thereof); viruses (analyte is, e.g., a viral coat protein, viral genome, or segment of viral genome, or antibody against the virus); other microorganisms (analyte is, e.g., a segment of the genome or the RNA of the microorganism, a toxin produced by the microorganism, or an heterologous protein made by the microorganism if it is genetically engineered) (with reference to protozoan parasites, see Lizardi and Noguiera, European Patent Application Publication No. 0 135 108); abnormal cells, such as cancer cells (analyte is, e.g., a cell surface antigen of the abnormal cell); or an abnormal gene (analyte is, e.g., a gene segment which includes the altered bases which render the gene abnormal, a messenger RNA segment which includes altered bases as a result of having been transcribed from the abnormal gene, or an abnormal protein product expressed from the abnormal gene). An analyte may also be a particular protein, such as, for example, a hormone, whose presence or concentration in serum or other body fluid is to be ascertained in an assay. In the case of immunoassays which entail the use of two antibodies, analyte may be antigen bound to first antibody (in the case of a sandwich assay) or first antibody bound to antigen (in the case of an immunosorbent assay). Many other types of analyte will be apparent to the skilled.

From the description of analyte, it is apparent that the present invention has widespread applicability, including in applications in which immunoassays or nucleic acid probe hybridization assays are employed. Thus, among other applications, the invention is useful in diagnosing diseases in plants and animals, including humans; and in testing products, such as food, blood, and tissue cultures, for contaminants.

An "affinity molecule" for an analyte is a molecule of an affinity substance (or, by a different name, a specific binding substance) for the analyte. Specific binding substances for particular analytes and methods of preparing them are well known in the art.

For an antigen analyte (which itself may be an antibody), antibodies, including monoclonal antibodies, are available as specific binding substances. For certain antibody analytes in samples which include only one antibody, an antibody binding protein such as Staphylococcus aureus Protein A can be employed as specific binding substance.

For an analyte which is a nucleic acid (DNA or RNA), or a segment thereof, oligonucleotides or polynucleotides (both also either DNA or RNA) which include a segment with a sequence complementary to that of a segment of the analyte are available as specific binding substances. Such affinity molecules can be made by any of numerous known in vivo or in vitro techniques, including automated synthesis techniques. As understood in the art, the length that a DNA or RNA affinity molecule must have to provide a predetermined specificity in an assay will depend in part on the amount and complexity of nucleic acid in the sample being assayed. Such an affinity molecule will usually require at least 10 nucleotides.

For an analyte, such as a glycoprotein or class of glycoproteins, or a polysaccharide or class of polysaccharides, which is distinguished from other substances in a sample by having a carbohydrate moiety which is bound specifically by a lectin, a suitable specific binding substance is the lectin.

For an analyte which is a hormone, a receptor for the hormone can be employed as a specific binding substance. Conversely, for an analyte which is a receptor for a hormone, the hormone can be employed as specific binding substance.

For an analyte which is an enzyme, an inhibitor of the enzyme can be employed as a specific binding substance. For an analyte which is an inhibitor of an enzyme, the enzyme can be employed as a specific binding substance.

Usually, an analyte molecule and an affinity molecule for the analyte molecule are related as a specific binding pair, i.e., their interaction is only through non-covalent bonds (e.g., salt-bridges, hydrogen-bonding, hydrophobic interactions).

The skilled can easily determine conditions whereby, in a sample, binding occurs between affinity molecule and analyte that may be present. In particular, the skilled can easily determine conditions whereby binding between affinity molecule and analyte, that would be considered in the art to be "specific binding," can be made to occur. As understood in the art, such specificity is usually due to the higher affinity of affinity molecule for analyte than for other substances and components (e.g., vessel walls, solid supports) in a sample. In certain cases, the specificity might also involve, or might be due to, a significantly more rapid association of affinity molecule with analyte than with other substances and components in a sample.

A sample on which the assay method of the invention is carried out can be a raw specimen of biological material, such as serum or other body fluid, tissue culture medium or food material. More typically, the method is carried out on a sample which is a processed specimen, derived from a raw specimen by various treatments to remove materials that would interfere with detection of analyte, such as by causing non-specific binding of affinity molecules. Methods of processing raw samples to obtain a sample more suitable for the assay methods of the invention are well known in the art.

Thus, the method can be carried out on nucleic acid from cells following the colony hybridization method of Grunstein and Hogness, Proc. Natl. Acad. Sci. (U.S.A.) 72, 3961–3965 (1975) (see also, e.g., Falkow and Moseley, U.S. Pat. No. 4,358,535; and Shafritz, U.S. Pat. No. 4,562,159) or the plaque lift method of Benton and Davis, Science 196, 180–182 (1977). It can also be carried out on nucleic acids isolated from viroids, viruses or cells of a specimen and deposited onto solid supports (Gillespie and Spiegelman, J. Mol. Biol. 12, 829–842 (1965)); including solid supports on dipsticks and the inside walls of microtiter plate wells. The method can also be carried out with nucleic acid isolated from specimens and deposited on solid support by "dot" blotting (Kafatos et al., Nucl. Acids Res. 7, 1541–1552 (1979); White and Bancroft, J. Biol. Chem. 257, 8569–8572 (1982); Southern blotting (Southern, J. Mol. Biol. 98, 503–517 (1975); "northern" blotting (Thomas, Proc. Natl. Acad. Sci. (U.S.A.) 77, 5201–5205 (1980); and electroblotting (Stellwag and Dahlberg; Nucl. Acids Res. 8, 299–317 (1980)). Nucleic acid of specimens can also be assayed by the method of the present invention applied to water phase hybridization (Britten and Kohne, Science 161, 527–540 (1968)) and water/organic interphase hybridizations (Kohne et al., Biochemistry 16, 5329–5341 (1977). Water/organic interphase hybridizations have the advantage of proceeding with very rapid kinetics but are not suitable when an organic phase-soluble linking moiety, such as biotin, is joined to the nucleic acid affinity molecule.

The assay method of the invention can also be carried out on proteins or polysaccharides isolated from specimens and deposited onto solid supports by dot-blotting, by "Western" blotting (see, e.g., Example XII), or by adsorption onto walls of microtiter plate wells or solid support materials on dipsticks.

Still further, the method of the invention is applicable to detecting cellular proteins or polysaccharides on the surfaces of whole cells (see, e.g., Example XI) from a specimen or proteins or polysaccharides from microorganisms immobilized on a solid support, such as replica-plated bacteria or yeast.

Either before or after affinity molecule is bound to analyte that might be present in a sample being assayed, a replicative RNA must be joined to the affinity molecule.

A "replicative RNA" can be any RNA capable of being autocatalytically replicated in vitro, i.e., replicated in vitro in a reaction catalyzed by an RNA-dependent RNA polymerase. Suitable RNA polymerases and suitable replicative RNAs for practice of the instant invention are described in Example I below.

In this connection, it is to be understood that reference herein to bacteriophage Q$\beta$ is not limited to any particular variant or mutant or population thereof. Such reference, unless otherwise specifically limited, is to any variant, mutant or population which, upon infection therewith of E. coli susceptible to bacteriophage Q$\beta$ infection, is capable of causing production of an RNA-dependent RNA-polymerase.

For other phages which, upon infection of bacteria susceptible to infection therewith, produce RNA-dependent RNA polymerases, and associated replicative RNAs capable of being autocatalytically replicated in vitro, which can be employed in the present invention, see, e.g., Miyake et al., Proc. Natl. Acad. Sci. (U.S.A.) 68, 2022–2024 (1971).

Replicative RNA can be joined to affinity molecule in numerous different ways, some of which are described in the Examples.

If replicative RNA is joined to affinity molecule prior to binding affinity molecule to analyte, it is, as the skilled will understand, essential that the specificity of the affinity molecule for analyte not be eliminated, i.e., the affinity molecule, joined to replicative RNA, must retain capability to bind with some specificity to the analyte to be tested for in an assay.

If replicative RNA is joined to affinity molecule after affinity molecule binds to analyte, it is essential, as the skilled will also understand, that affinity molecule with replicative RNA joined be capable of being separated from replicative RNA that has not joined to affinity molecule. This is not a significant problem. In the usual case, with affinity molecule bound to analyte bound in turn to a solid support, such separation is readily accomplished by simple washing, because joining of replicative RNA to bound affinity molecule does not significantly disrupt the connection of affinity molecule to solid support. If the usual case does not obtain, such separation can be readily accomplished by any of several well known chromatographic and electrophoretic techniques.

Finally, the joining of replicative RNA to affinity molecule must be such that the replicability of the RNA by a RNA-dependent RNA polymerase is not eliminated, i.e., either the replicative RNA, as joined to affinity molecule, is a template for replication by an RNA-dependent RNA polymerase or is capable of being severed from the affinity molecule to a form which is a template for replication by an RNA-dependent RNA polymerase.

In one type of connection between replicative RNA and affinity molecule, the affinity molecule itself is a replicative RNA, namely a recombinant RNA which includes a segment with an appropriate sequence. Such an affinity molecule will be for an analyte which is a nucleic acid or segment thereof. The affinity molecule will be a recombinant RNA prepared from a replicative RNA, preferably by the procedure of Miele et al., supra, and Kramer et al., U.S. patent Application Ser. No. 614,350, supra, to include a segment with a sequence complementary to that of a segment of the analyte. This segment of complementary sequence will be at least 10 ribonucleotides in length, to provide specificity, and can be up to about 4500 nucleotides in length without eliminating replicability. Example IX illustrates use of a recombinant replicative RNA as an affinity molecule.

The connection between replicative RNA and affinity molecule can be non-covalent or covalent.

A non-covalent connection between affinity molecule and replicative RNA can be effected by joining to or including in affinity molecule a nucleic acid segment of sequence complementary to that of a segment of replicative RNA and hybridizing the replicative RNA to the segment joined to or included in affinity molecule. For joining such a nucleic acid segment to an affinity molecule which is a protein, see, e.g., Dattagupta et al., European Patent Application Publication No. 0 154 884. For an affinity molecule which is a nucleic acid, methods of joining or including such a segment are well known in the art. With such a connection between affinity molecule and replicative RNA, separation of replicative RNA from affinity molecule bound to analyte, to enable the replicative RNA to be replicated for detection, is accomplished by heating above the melting temperature of the complex between replicative RNA segment and nucleic acid segment joined to or included in affinity molecule.

A non-covalent connection between replicative RNA and affinity molecule can also be effected through binding of a first linking moiety, joined to replicative RNA, and a second linking moiety, joined to affinity molecule, said linking moieties being related as a specific binding pair.

A covalent connection between replicative RNA and affinity molecule is through bonds between the two which (but for bonds arising from secondary or tertiary structure in the complex) are only covalent. Usually a covalent connection involves a first linking moiety, which is covalently joined to replicative RNA; a second linking moiety, which is covalently joined to affinity molecule; and a covalent connection between the first and the second linking moiety.

Reference herein to "covalent joining" or "covalent linkage" or "covalent connection" of a linking moiety to a replicative RNA or an affinity molecule means that all bonds between the linking moiety and the replicative RNA or affinity molecule, respectively, other than bonds arising from secondary or tertiary structure, are covalent. Reference herein to "joining" or "linkage" or "connection" of a linking moiety to a replicative RNA or an affinity molecule, without qualification, means that the linking moiety is either "covalently" or "non-covalently" joined or linked to the replicative RNA or affinity molecule, respectively. "Non-covalent" joining or linkage or connection means that at least some bonds, other than bonds due to secondary or tertiary structure, between linking moiety and replicative RNA or affinity molecule are non-covalent.

Examples of covalent linkages between linking moiety and replicative RNA, whereby the replicability of the RNA is not eliminated, include, among others, the following:

(a) Linking moiety is a phosphate group and linkage is directly between the phosphate and the 5'-carbon of the 5'-nucleotide of replicative RNA. The phosphate linking moiety, bonded to the 5'-carbon of the 5'-nucleotide of replicative RNA, will usually be involved in covalently joining a replicative RNA directly to the 3'-carbon of the 3'-nucleotide of a nucleic acid affinity molecule or to the 3'-carbon of the 3'-nucleotide of a segment of nucleotides which is a linking moiety considered to be bonded to the 3'-end of a nucleic acid affinity molecule and which is covalently joined, through a phosphte at the 5'-carbon of its 5'-nucleotide, to the 3'-carbon of the 3'-nucleotide of the affinity molecule. The 5'-terminal nucleotide of a replicative RNA can be phosphorylated at the 5'-carbon with T4 polynucleotide kinase by methods known in the art. See also Example I. Affinity molecule, or nucleic acid linking moiety of affinity molecule, can then be connected to the 5'-phosphate of the 5'-nucleotide of replicative RNA by known methods employing T4 RNA ligase. This latter reaction proceeds more efficiently if a ribonucleotide is at the 3'-terminus of the affinity molecule (or linking moiety of affinity molecule); as known in the art, a single ribonucleotide can be attached to the 3'-terminus of a DNA with terminal deoxynucleotidyl transferase.

(b) Linking moiety is biotinyl or iminobiotinyl and linkage is to the 5'-carbon of the 5'-nucleotide of replicative RNA through a spacer group of formula $—NH(CH_2)_{aa}NH(PO_2)O—$, formula $—NH(CH_2)_{bb}SS(CH_2)_{cc}NH(PO_2)O—$, or formula $—HN(CH_2)_{bb}(CO)(NH)(CH_2)_{cc}NH(PO_2)O—$ wherein, in each case, the phosphoramidate group is bonded to the 5'-nucleotide and the amino group to the biotinyl or iminobiotinyl, aa is 2 to 20, and bb and cc are the same or different and are each 2 to 10. Replicative RNA with spacer group of formula $—NH(CO_2)_{aa}NH(PO_2)O—$ can be made following the teaching of Chu and Orgel, DNA 4, 327–331 (1985). Replicative RNA with spacer group of formula $—NH(CH_2)_{bb}SS(CH_2)_{cc}NH(PO_2)O—$ is taught in Example I. Replicative RNA with spacer group of formula $—NH(CH_2)_{bb}(CO)(NH)(CH_2)_{cc}NH(PO_2)O—$ is made by reacting replicative RNA, with group of formula $—O(PO_2)NH(CH_2)_{cc}NH_2$ bonded to the 5'-carbon of the 5'-nucleotide, with an active ester of the aminocarboxylic acid of formula $NH_2(CH_2)_{bb}CO_2H$. Reaction of N-hydroxysuccinimo ester of biotin or iminobiotin to form a biotin-amide or iminobiotin-amide linkage with a primary amino group is known in the art and taught in the Examples.

(c) An amino group linking moiety linked through a spacer group of formula $—(CH_2)_{aa}(NH)(PO_2)O—$ or $—(CH_2)_{bb}SS(CH_2)_{cc}NH(PO_2)O—$, wherein the phosphoramidate group is linked to the 5'-carbon of the 5'-nucleotide of the replicative RNA and wherein aa, bb and cc are as defined supra. The methods of Chu and Orgel, DNA 4, 327–331, and of Example I below, can be employed to prepare such replicative RNAs.

(d) A sulfur linking moiety joined by a spacer group of formula $—(CH_2)_{cc}NH(PO_2)O—$, wherein the phosphoramidate group is bound to the 5'-carbon of the 5'-nucleotide of replicative RNA and cc is as defined above. Examples I and X teach synthesis of a replicative RNA with such a linking moiety and spacer group.

An example of a "non-covalent" linkage between a linking moiety, avidin or streptavidin, and replicative RNA would be the linkage wherein the avidin or streptavidin is complexed with biotinyl or iminobiotinyl (said complex involving only non-covalent interactions) and the biotinyl or iminobiotinyl, in turn, is connected to the 5'-carbon of the 5'-nucleotide of the replicative RNA by one of the spacer groups described above for covalently joining biotinyl or iminobiotinyl to replicative RNA.

For affinity molecules which are nucleic acids, covalent linkages with linking moieties can be made through the 5'-carbon of the 5'-nucleotide, the 3'-carbon of the 3'-nucleotide, or various atoms of pyrimidine or purine bases. A linking moiety might be a nucleotide at the 3' or 5'-terminus of a segment of nucleic acids extending from the 3' or the 5'-terminus, respectively, of the segment of the affinity molecule with sequence complementary to that of a segment of analyte. A linking moiety might be, for example, a biotinyl or iminobiotinyl, or a sulfur atom, joined to the 5'-carbon of the 5'-nucleotide of the affinity molecule by one of the spacer groups described above for joining such linking groups to the 5'-carbon of the 5'-nucleotide of replicative RNA. Biotinyl linking moiety (or moieties) might be joined through any of various spacer arms to the 5-carbon of a uracil moiety (or moieties) or the 8-carbon or 6-carbon of an adenine moiety (or moieties) in a portion of nucleic acid affinity molecule outside the segment with sequence complementary to the sequence of the segment of analyte with which affinity molecule hybridizes to analyte. See, e.g., Ruth, Patent Cooperation Treaty Publication No. 84/03285; Brakel and Stavrianopoulous, European Patent Application Publication No. 0 122 614. As with replicative RNAs, numerous other linking moieties and spacer groups, suitable for affinity molecules, particularly in that they do not eliminate the specificity of affinity molecule for analyte, and methods of preparing affinity molecules with such linking moieties and spacer groups are known in the art.

For affinity molecule which are antibodies, antigens or lectins, numerous linking moieties (e.g., biotinyl, nucleic acid segment for hybridization to replicative RNA, sulfur atom) and means for suitably covalently linking them to affinity molecule, directly or through spacer groups, are known in the art. Many biotinylated antibodies and lectins, for example, are available commercially.

One example of a "non-covalent" linkage between a linking moiety, avidin or streptavidin, and an antibody, antigen or lectin affinity molecule would be the linkage wherein the avidin or streptavidin is complexed with biotin or iminobiotin, which in turn is linked non-covalently or covalently to affinity molecule. Biotin, for example, could be non-covalently linked to an antibody affinity molecule by complexing biotinylated anti-antibody or biotinylated S. aureus Protein A with the antibody affinity molecule, as understood in the art.

Among additional information in the art relating to joining linking moieties to proteins and nucleic acids see, e.g., Dreyer and Dervan, Proc. Natl. Acad. Sci. (U.S.A.) 82, 968–972 (1985); Forster et al., Nucl. Acids Res. 13, 745–761 (1984); Ward et al., European Patent Application Publication No. 0 063 879; Englehardt et al., European Patent Application Publication No. 0 097 373; Alagon and King, Biochemistry 19, 4341–4345 (1980); Imam et al., Cancer Res. 45, 263–271 (1985).

A first linking moiety, joined to replicative RNA, and a second linking moiety joined to affinity molecule, effect the connection between replicative RNA and affinity molecule by being covalently joined to each other (such as in a disulfide moiety formed from two sulfur atom linking moieties, or in a stretch of nucleotides from the 3'-end of nucleic acid affinity molecule joined to a phosphate at the 5'-end of a replicative RNA) or by interacting with each other non-covalently as a specific binding pair (such as biotin or iminobiotin joining with avidin or streptavidin, or an antigen joining with a corresponding antibody, or an enzyme inhibitor joining with the enzyme.

As indicated, supra, one example of a covalent linkage between affinity molecule and replicative RNA is linkage effected through a stretch of purine residues added at the 3'-end of a DNA affinity molecule, either during in vitro synthesis of the affinity molecule or employing terminal deoxynucleotidyl transferase, and then joining the replicative RNA, through its 5'-end, to the 3'-end of the stretch of (one or more) purines employing T4 RNA ligase. As understood in the art, the purine nucleoside at the 3'-end of this linking segment should be a ribonucleoside for the attachment to replicative RNA to proceed efficiently. After such an affinity molecule-replicative RNA hybrid is bound to analyte, if is is not active as a template for RNA replicase, the RNA can be cleaved from the DNA, by acid depurination followed by B-elimination to cleave the phosphodiester bond, and then employed as a template for the replicase.

Another example involves joining an RNA affinity molecule to either end of a replicative RNA employing T4 RNA ligase. Such a molecule is prepared so that it has several ribonucleotides between the replicative RNA and the segment of the affinity molecule which hybridizes to analyte. The resulting RNA may itself be a template for an RNA replicase, if the affinity molecule RNA is appended to the 5'-end of the replicative RNA. If the resulting RNA is not a template for the replicase, the affinity molecule portion is cleaved from the replicative RNA portion to release replicative RNA. Such cleavage is accomplished by first hybridizing to the molecule (hybridized to analyte or freed by heating (or otherwise melting) after hybridizing to analyte) an oligodeoxyribonucleotide with sequence complementary to the segment between replicative RNA and the portion of affinity molecule which hybridizes to analyte and then cleaving with ribonuclease H, which cleaves RNA specifically where it is hybridized to DNA. See Donis-Keller, Nucl. Acids Res. 7, 179–192 (1979).

Among affinity molecule-replicative RNA hybrid compounds (i.e., a compound in which an affinity molecule is joined to a replicative RNA) according to the invention are "smart probes." A "smart probe" is an affinity molecule-replicative RNA hybrid wherein the affinity molecule is a nucleic acid, the second linking moiety is covalently joined to the affinity molecule, the first linking moiety is covalently joined to replicative RNA, and first and second linking moieties are covalently joined to each other (i.e., all bonds, excluding bonds due to secondary or tertiary structure, between the two linking moieties are covalent). Further, in a smart probe, the affinity molecule, and first and second linking moieties joining the two, and any moiety linking the two linking moieties, are designed so that, ideally, replicative RNA of a hybrid is replicated by an RNA-dependent RNA polymerase if and only if the affinity molecule portion is hybridized to its analyte. In effect, the probe is "smart" because it makes itself detectable by binding to analyte.

In one embodiment of a smart probe according to the invention, the replicative RNA portion is a recombinant replicative RNA which includes a short segment, of about 10 to about 30 ribonucleotides, with a sequence complementary to the sequence of a segment at the 3'-end of the affinity molecule portion. The recombinant replicative RNA is made by, for example, the method of Miele et al., supra, and Kramer et al., U.S. patent application Ser. No. 614,350, supra. The affinity molecule portion is typically about 75 to 150 nucleotides in length, somewhat longer than the segment with sequence complementary to the sequence of the segment recombined into the replicative RNA portion, and is made by any of numerous in vitro and in vivo methods known in the art. The 5'-carbon of the 5'-nucleotide of the recombinant replicative RNA portion and the 5'-carbon of the 5'-nucleotide of the affinity molecule portion are joined in the smart probe, following methods of Example I and X, by a moiety of formula $—O(PO_2)NH(CH_2)_aSS(CH_2)_bNH(PO_2)O—$, wherein a and b are the same or different and are each 2 to 20. In such a smart probe, the 3'-end of the affinity molecule portion remains hybridized to the recombinant replicative RNA portion unless the affinity molecule portion becomes more stably associated with something else; such an association will be virtually only specific binding with analyte or non-specific binding. In using the probe: hybridization is first carried out with nucleic acid of a sample; then a solution of ribonuclease H is added, which results in cleavage and elimination of replicability of the replicative RNA portion of any smart probe in which affinity molecule portion has not dissociated from replicative RNA portion (see Donis-Keller, (1979), supra); then a brief washing is carried out to eliminate unbound smart probe and further reduce the small amount of non-specifically bound smart probe in which affinity molecule portion happened to dissociate from replicative RNA so that the replicative RNA escaped cleavage with ribonuclease H; and finally, optionally after cleaving the disulfide with dithiothreitol to sever replicative RNA from affinity molecule, detection is accomplished by replicating the RNA and detecting replicated RNA.

In another embodiment of a smart probe of the invention, ribonuclease H cleavage is not required to inactivate replicative RNA of probe not hybridized to target. In this embodiment, the 5'-carbon of the 5'-nucleotide of the affinity molecule portion is, like in the other embodiment, connected to the 5'-carbon of the 5'-nucleotide of the replicative RNA portion by a moiety of formula $—O(PO_2)NH(CH_2)_aSS(CH_2)_bNH(PO_2)O—$. In this embodiment, any replicative RNA can be employed; it is not necessary to prepare a recombinant replicative RNA to correspond to the affinity molecule portion. However, in this embodiment the affinity molecule portion consists essentially of three segments: an "analyte-binding" segment, which has about 50 to about 150 nucleotides in a sequence complementary to that of the segment of analyte to which the affinity molecule hybridizes; a "5'-clamp" segment, which extends from the 5'-nucleotide of the affinity molecule to (but not including) the 5'-nucleotide of the analyte-binding segment and has about 30 to about 60 nucleotides in a sequence complementary to that of a segment of the replicative RNA; and a "3'-clamp" segment, which extends from (but does not includes) the 3'-nucleotide of the analyte-binding segment to the 3'-nucleotide of the affinity molecule and has about 30 to about 60 nucleotides in a sequence complementary to that of a segment of the replicative RNA closer to the 5'-end of the replicative RNA than the segment to which the 5'-clamp segment of affinity molecule hybridizes. Optionally, in this embodiment, by methods known in the art, at least some of the guanosine bases in the segments of replicative RNA which hybridize to the 5'-clamp segment and 3'-clamp segment of the affinity molecule can be replaced with inosines; the effect of this will be to leave (unclamped) replicative RNA active as a template for replication and stabilize DNA-RNA and destabilize RNA-RNA base-pairing with these segments of replicative RNA. The affinity molecule in this embodiment, as in the other, is made by any known in vitro or in vivo methods. The linking of replicative RNA portion to affinity molecule portion is accomplished following Examples I and X. In this embodiment, the replicative RNA is "clamped" in a non-replicable form, inactive as a template for replication, as long as both the 3'-clamp segment and the 5'-clamp segment of affinity molecule are hybridized to replicative RNA. Once the smart probe encounters something, with which the affinity molecule portion binds with sufficient stability, which will be virtually only analyte, so that one or the other of the clamp segments releases from replicative RNA, the RNA snaps into a replicable and detectable form. In using this embodiment of a smart probe of the invention: hybridization is first carried out with nucleic acid of a sample; then a brief washing is carried out to eliminate unbound smart probe and reduce further the small amount of non-specifically bound smart probe in which one or both of the clamp segments is released from replicative RNA; finally, optionally after cleaving the disulfide with dithiothreitol to sever replicative RNA from affinity molecule, detection is accomplished by replicating the RNA and detecting replicated RNA.

Because signals arising from non-specific binding of replicative RNA to sites which do not contain analyte will be reduced with smart probes according to the invention, the need for prolonged post-hybridization washing to achieve acceptably low background will be reduced in assays with such probes, in comparison with typical nucleic acid probe hybridization assays currently used in the art.

After the necessary binding and washing steps are carried out, as the skilled in the immunoassay and nucleic acid probe hybridization assay arts will understand, so that, but for unavoidable "non-specific binding" of affinity molecule or replicative RNA (via the RNA portion or first linking moiety portion thereof), which give rise to "background," only replicative RNA associated with analyte (through being joined or having been joined with affinity molecule) is present in an assay system, the system is subjected to conditions whereby the replicative RNA is made detectable by a process comprising replication with an RNA-dependent RNA polymerase.

It is necessary for carrying out assays according to the instant invention that replicative RNA, joined to affinity molecule that is or has been bound to analyte in an assay, be capable of being replicated by an RNA-dependent RNA polymerase either while joined to affinity molecule or after being severed therefrom. Various means of severing replicative RNA from affinity molecule are described supra, including reductive cleavage of disulphide bonds in or between linking moieties joining replicative RNA to affinity molecule.

Methods for replicating replicative RNAs with RNA-dependent RNA polymerases are known in the art. Generally, the RNA must simply be combined with the enzyme in a suitable aqueous buffer containing the four ribonucleoside-5'-triphosphates, ATP, CTP, GTP and UTP, and incubated at a suitable temperature. The examples provide suitable conditions for replication with the preferred enzyme, $Q\beta$ replicase. See also Kramer et al., J. Mol. Biol. 89, 719–736 (1974); Kramer et al., U.S. patent application Ser. No. 614,350; Miele et al. (1983), supra.

Alternatively, replicative RNA cleaved from affinity molecule can be bound to a positively charged support, such as ECTEOLA paper (Saris et al., Nucl. Acids Res. 10, 4831–4843 (1982). Such a support, with bound replicative RNA, is suspended in a solution of the RNA replicase (RNA-dependent RNA polymerase) with suitable buffer and the four ribonucleoside-5'-triphosphates and at suitable temperature (i.e., essentially the same conditions that would be employed for solution-phase replication), and replication of the support-bound RNA takes place. See Saris et al. (1982), supra; and Bresser et al., Proc. Natl. Acad. Sci. (U.S.A.) 80, 6523–6527 (1983). Conveniently for detection of the RNA, replicated RNA remains bound to the positively charged support.

The replicated RNA can be detected in a number of different ways:

Detection can be by ultraviolet absorbance of replicated RNA, as, for example, by the method of contact photoprinting (Kutateladze et al., Anal. Biochem. 100, 129–135 (1979)).

By employing a radioactively labeled ribonucleoside-5'-triphosphate in the replication reaction (e.g., $^3H$-labeled or alpha-$^{32}PO_4$-labeled), so that the replicated RNA is radioactive, the replicated RNA can be detected, by any of numerous known procedures, by means of its radioactivity.

Biotin or iminobiotin can be incorporated into replicated RNA, which can then be detected by known techniques with an enzyme-avidin or enzyme-streptavidin adduct, which binds to the RNA-bound biotin and catalyzes production of a conveniently detectable chromogen. See Matthews et al. (1985), supra; Leary et al. (1983), supra; Ward et al., supra; and Englehardt et al., supra. Incorporation of biotin or iminobiotin into replicated RNA can be accomplished by employing UTP that is biotinylated through a spacer to carbon-5 of the uracil moiety as a substrate for the replicase in the replication reaction. Such UTP's are known compounds. Further, it is known that such UTP's are substrates for Qβ replicase, and that RNAs which include uracils biotinylated through spacer groups joined to the carbon-5 position, due to use of such UTP's in their synthesis, are templates for Qβ replicase catalyzed replication.

RNA resulting from the replication process could also be biotinylated employing photobiotin acetate according to the procedure of Forster et al., (1985), supra, and then detected, with an avidin-enzyme adduct-chromogenic compound system, like replicated RNA's synthesized with biotinylated UTP in the replication reaction.

RNA resulting from the replication process can be made fluorescent by employing a T4 RNA ligase catalyzed reaction to append nucleotides modified to be fluorescent to the 3'-end of replicative RNA. See Cosstick et al., Nucl. Acis Res. 12, 1791–1810 (1984). The fluorescence of the resulting RNA can be employed to detect the RNA by any of several standard techniques.

Among still other methods that can be used to detect replicated RNA are those wherein a reporter substance, that binds specifically with nucleic acid, is added to the system in which the replication has taken place, or to the medium, such as a positively charged support such as ECTEOLA paper, on which replicated RNA has been isolated, and signal from the reporter substance measured. Such substances include: chromogenic dyes, such as "stains all" (Dahlberg et al., J. Mol. Biol. 41, 139–147 (1969); methylene blue (Dingman and Peacock, Biochemistry 7, 659–668 (1968), and silver stain (Sammons et al., Electrophoresis 2, 135–141 (1981); Igloi, Anal. Biochem. 134, 184–188 (1983)); fluorogenic compounds that bind to RNA—for example, ethidium bromide (Sharp et al., Biochemistry 12, 3055–3063 (1973); Bailey and Davidson, Anal. Biochem. 70, 75–85 (1976); and fluorogenic compounds that bind specifically to RNAs that are templates for replication by Qβ replicase—for example, a phycobiliprotein (Oi et al., J. Cell Biol. 93, 981–986 (1982); Stryer et al., U.S. Pat. No. 4,520,110) conjugated to the viral subunit of Qβ replicase.

Provided that the concentration of replicase remains above the concentration of template RNA, and that ribonucleoside-5'-triphosphate concentration does not become limiting, the concentration of template RNA will increase exponentially with time during replicase-catalyzed RNA replication. After template RNA concentration equals or exceeds replicase concentration, as long as ribonucleoside-5'-triphosphate concentration does not become limiting, the concentration of template RNA will increase linearly with time. See, e.g., Kramer et al. (1974), supra.

It has been found that, under the conditions for replicase-catalyzed replication specified in Example I, the MDV-1 RNA there exemplified doubled in concentration every 36 seconds, until template concentration exceeded enzyme concentration.

The concentration of template RNA, in a replicase-catalyzed replication reaction system after a given time for reaction, will be related to the initial concentration of template RNA. If, at all times during the replication reaction, the concentration of replicase exceeds that of template (and ribonucleoside-5'-triphosphate concentration does not become limiting), the log of concentration of template RNA at the conclusion of the reaction will be directly proportional to the log of the initial concentration of template (at the start of the reaction). After replicase concentration falls below template concentration, as long as ribonucleoside-5'-triphosphate concentration does not become limiting, the concentration of template at the conclusion of reaction is directly proportional to the log of the initial concentration of template. Further, the time required for a reaction to reach the point at which template concentration equals replicase concentration is proportional to the negative log of the initial concentration of template.

By allowing the replication reaction to proceed for longer times, greater sensitivity can be achieved.

In assays according to the invention, assays are carried out simultaneously, under conditions as nearly alike as possible, on both test samples, which are being tested for analyte, and control samples. As understood in the art, control samples are similar to test samples but are known to contain either no analyte or a known quantity of analyte. A control with no analyte establishes the "background," below which it is not possible to distinguish samples which contain analyte from those which do not. By comparing the amount or concentration of replicated replicative RNA produced in an assay of a test sample with the amount or concentration produced with control samples assayed simultaneously, the presence of analyte in test sample at a level above background can be determined. If control samples with a range of known concentrations of analyte are employed, the concentration of analyte in a test sample can be estimated.

The invention will now be described in greater detail by way of examples.

EXAMPLE I

This Example shows the joining of biotin and then avidin to a mutant midivariant RNA (referred to as "MDV-1" RNA) in a manner such that the RNA remains active as a template for Qβ RNA polymerase and is severable from the biotin or biotin plus avidin. By virtue of its ability to bind specifically to avidin, through a biotin-avidin specific binding pair, the MDV-1 RNA with only biotin attached is a universal reporter for any affinity molecule to which an avidin moiety can be joined (e.g., through a biotin that itself is linked directly to the affinity molecule) without eliminating the affinity molecule's ability to bind specifically to its target biopolymer analyte. By virtue of its ability to bind specifically to biotin and thereby, because of the specific binding pair relationship between biotin and avidin, MDV-1 RNA with both the biotin and avidin (complexed to the biotin) attached may be used as a universal reporter for any affinity molecule to which a biotin moiety can be attached without eliminating the biotin moiety's own ability to bind specifically to avidin or the affinity molecule's ability to bind specifically to its target biopolymer analyte. (Avidin has four biotin-reactive sites and may, therefore, be the middle component of a biotin-avidin-biotin linkage.)

MDV-1 RNA has the same sequence as the mutant midivariant RNA shown in Miele et al., J. Mol. Biol. 171, 281–295 (1983), with the following differences. The C at position 43 of the Miele et al. sequence is changed to a U in the MDV-1 RNA. The A at position 61 of the Miele et al. sequence is changed to a G in MDV-1 RNA. The A at position 105 in the Miele et al. sequence is changed to a U in MDV-1 RNA. The C at position 134 of the Miele et al. sequence is changed to a U in MDV-1 RNA. Finally, the G at position 135 in the sequence of Miele et al. is changed to a A in the sequence of MDV-1 RNA. Although a particular mutant RNA, with the sequence just described, was used in this and other examples of the present specification, this mutant was used merely because a supply was conveniently available. Any RNA that is a template for replication in vitro by the Qβ replicase, including "wild-type" midivariant RNA, mutants of midivariant RNA different from MDV-1 RNA, minivariant RNA, microvariant RNA, one of the nanovariant RNAs, other variants that have been identified but to which names have not yet been assigned, or mutants of any of the foregoing, that retain the capability to be replicated by the Qβ replicase in vitro, could have been used as well.

Further, although the Qβ RNA-dependent RNA polymerase is the preferred replicase for the present invention, on account of its remarkable stability in vitro, there are numerous other RNA-dependent RNA polymerases known in the art which could be employed, together with replicative RNAs which they recognize as templates for replication. Among these other enzymes are the SP replicase and the MS2 replicase.

5′-pppMDV-1 (+) RNA, obtained by enzymatic synthesis with Qβ replicase, was converted to a 5′-biotinylated MDV-1 (+) RNA-avidin adduct in a series of steps: (1) the 5′-terminal triphosphate group was removed by incubation with calf intestine alkaline phosphatase and replaced with a 5′-terminal monophosphate by incubation with [gamma-$^{32}$P]ATP and T4 polynucleotide kinase; (2) a 5′-phosphoroimidazole group was created by condensation with imidazole in the presence of the coupling reagent, 1-ethyl-3-[3-dimethylamino-propyl] carbodiimide; (3) the imidazole group was replaced with a cystamine group by incubation with cystamine dihydrochloride; (4) biotin was linked to the cystamine by incubation with the biotinylating agent, N-hydroxysuccinimidobiotin; and (5) avidin was bound to the 5′-biotin group by incubation with avidin. Also, (6) the 5′-biotinylated MDV-1 RNA-avidin adduct was separated from partially reacted intermediates by acrylamide gel electrophoresis. The first four steps of the following reaction sequence summarize steps 2–5 described above:

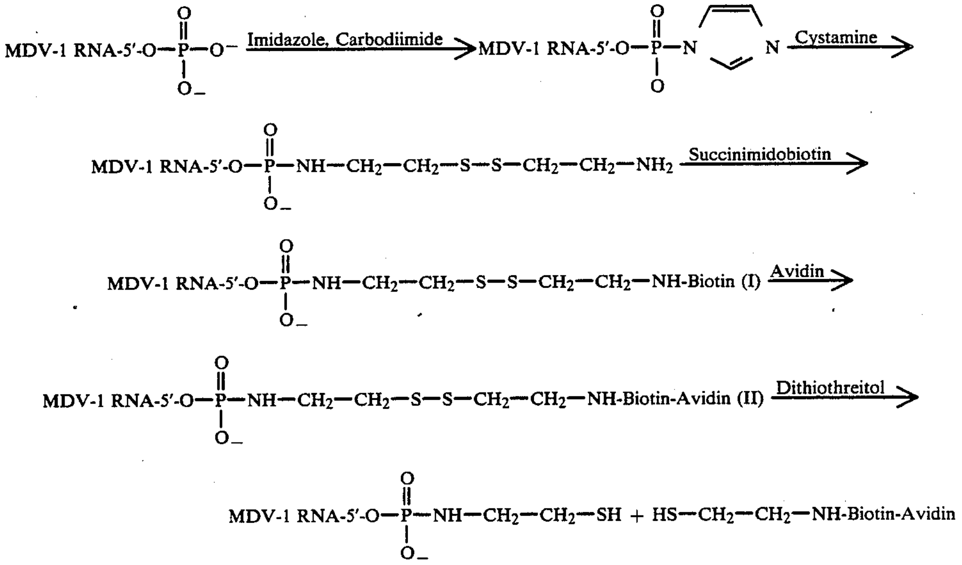

The fifth step shown in the sequence shows reductive cleavage of the disulfide of the cystamine moiety to separate RNA from biotin-avidin, as discussed below.

The electrophoretic mobility of the RNA-biotin-avidin adduct (II) was lower than the mobility of the 5′-biotinylated RNA precursor (I), due to its larger size. The amount of RNA-biotin-avidin adduct formed (determined by measuring the radioactivity in each gel band) increased asymptotically as a function of avidin concentration, reaching a maximum at 25–35% adduct formed. The identity of the RNA-biotin-avidin adduct (II) was confirmed in three ways: (1) the 5'-cystamine MDV-1 RNA was incubated with avidin and the electrophoretic mobility of the product was identical to the mobility of an unreacted control, indicating that the adduct in the slower migrating band was not the unbiotinylated precursor; (2) similarly, the 5'-phosphorylated MDV-1 RNA was reacted with the biotinylation agent, purified by electrophoresis, incubated with avidin, and its mobility remained the same; and (3) more than 80% of the adduct eluted from the slower-migrating band bound to biotinylated agarose, while less than 10% of a control containing the 5'-cystamine adduct was bound.

More specifically, the attachment of biotin and avidin to the 5' end of MDV-1 (+) RNA and identification of the adducts were performed using materials and according to methods as follows:

Enzymes and Chemicals

The following were purchased: calf intestine alkaline phosphatase (Boehringer Mannheim Biochemicals, Indianapolis, Ind., U.S.A.), bacteriophage T4 polynucleotide kinase (Pharmacia P-L Biochemicals, Piscataway, N.J., U.S.A.); ribonuclease T1 and highly polymerized yeast RNA (Calbiochem-Behring, San Diego, Calif., U.S.A.); N-hydroxysuccinimidobiotin (Sigma Chemical Co., St. Louis, Mo., U.S.A.); 2,2'-dithiobis(ethylamine)-dihydrochloride (CTC Organics, Atlanta, Ga., U.S.A.; 1-ethyl-3-[3-dimethylaminopropyl] carbodiimide (Aldrich Chemical Co., Milwaukee, Wisc., U.S.A.); biotinylated agarose (binds 8 mg avidin/ml) and avidin DN (Vector Laboratories, Burlingame, Calif., U.S.A.); and [gamma-$^{32}$P]ATP and [alpha-$^{32}$P]GTP (Amersham, Arlington Heights, Ill., U.S.A.). Q$\beta$ RNA replicase was isolated from bacteriophage Q$\beta$-infected Escherichia coli Q13 by the procedure of Eoyang and August (L. Eoyang et al., (1971) in Procedures in Nucleic Acid Research, eds. G. L. Cantoni & D. R. Davies (Harper and Row, New York), Vol. 2, pp. 829-839), with the hydroxyapatite step omitted.

Preparation of MDV-1 (+) RNA

A readily identifiable and isolatable (see Kramer et al., J. Mol. Biol. 89, 719-736 (1974)) mutant of midivariant RNA is employed in the examples and is referred to herein as "MDV-1 RNA." Its sequence is described supra. 758 ug of MDV-1 RNA were synthesized by incubating 705 ng of mutant MDV-1 (+) RNA template and 69 ug Q$\beta$ replicase for 210 minutes at 37° C. in 1 ml containing 1 mM ATP, 1 mM CTP, 1 mM GTP, 1 mM UTP, 15 mM $MgCl_2$, 100 mM Tris-HCl, pH 7.5 The incubation mixture was then deproteinized by extraction with phenol (K. S. Kirby (1968) in Methods in Enzymology, eds. L. Grossman & K. Moldave (Academic Press, New York), Vol. 12, part B, pp. 87-100) and the RNA was isolated by precipitation with 2 volumes of ethanol at −20° C. in the presence of 2 M ammonium acetate. MDV-1 (+) RNA was separated from MDV-1 (−) RNA by acrylamide gel electrophoresis in the presence of 1 mM $MgCl_2$ (D. R. Mills, et al., Cell 15, 541-550 (1978)).

Analysis and Isolation of Chemically Modified RNAs

RNA intermediates were isolated from reaction mixtures by spin column chromatography through Sephadex G-50 (Pharmacia P-L Biochemicals) equilibrated in 100 mM NaCl, 1 mM EDTA, 10 mM Hepes, pH 7.5 (T. Maniatis et al., Molecular Cloning: A Laboratory Manual, Cold Spring Harbor Press, Cold Spring Harbor, New York, 1982). RNAs were precipitated from solution by the addition of 2 volumes of ethanol at −20° C. in the presence of 100 mM NaCl. Electrophoresis was carried out on 1 mm thick 6% polyacrylamide gels cast and run in 90 mM Tris-borate, pH 8.3, 1 mM EDTA. Denaturing gels also contained 7 M urea. Prior to electrophoresis on denaturing gels, RNAs were melted by heating for 1 minute at 90° C. in 7 M urea and immediately chilled. Autoradiographs of gels were obtained by exposure to Kodak X-Omat AR film at −80° C., with or without a DuPont Cronex Lightning Plus intensifying screen. RNAs were eluted from gels with 500 mM ammonium acetate, pH 7.5, 1 mM EDTA (T. Maniatis et al., supra).

Dephosphorylation of 5'-pppMDV-1 (+) RNA

The 5'-terminal triphosphate groups were removed from 2 ug of MDV-1 (+) RNA by incubation with 0.7 EU calf intestine alkaline phosphatase for 30 minutes at 50° C. in 50 ul 50 mM Tris-HCl, pH 8, 100 uM EDTA. Another 0.7 EU calf intestine alkaline phosphatase was added and the incubation was continued for an additional 30 minutes. The reaction was terminated by bringing the incubation mixture to 100 mM NaCl and 2% sodium dodecyl sulphate and heating it for 5 minutes at 60° C. The solution was then deproteinized by extracting it twice with phenol:chloroform (1:1) and twice with chloroform (T. Maniatis et al., supra). The dephosphorylated MDV-1 RNA was then isolated by precipitation with ethanol.

5'-$^{32}$P Phosphorylation of MDV-1 RNA 2 ug of dephosphorylated MDV-1 RNA were incubated for 3 minutes at 50° C. in 20 ul 10 mM Tris-HCl, pH 7.5, 1 mM spermidine, 100 uM EDTA, and were then chilled rapidly. The volume was then brought to 40 ul with the addition of 12.2 pmol [gamma-$^{32}$P]ATP (300 Ci/mmol), 30 EU T4 polynucleotide kinase, and buffer to a final concentration of 10 mM $MgCl_2$, 1 mM dithiothreitol, 50 mM Tris-HCl, pH 7.5. This solution was incubated for 75 minutes at 37° C., and the reaction was stopped by bringing the mixture to.20 mM EDTA. The kinase was extracted with an equal volume of phenol:chloroform (1:1) and the phosophorylated MDV-1 RNA was isolated by precipitation with ethanol. The RNA was purified further by spin column chromatography through Sephadex G-50, followed by reprecipitation with ethanol, and then it was suspended in 1 mM EDTA-NaOH, pH 8.

Conversion of MDV-1 RNA to 5'-cystamine-MDV-1 RNA 2 ug of [5'-$^{32}$P]MDV-1 RNA and 16 ug of highly polymerized yeast RNA (previously dephosphorylated by incubating 180 ug yeast RNA with 50 EU calf intestine alkaline phosphatase for 1 hour at 50° C.) were incubated for 3 minutes at 50° C. in 20 ul of 1 mM EDTA-NaOH, pH 8, and then immediately chilled. 2.5 ul of 1 M imidazole, pH 6, and 2.5 ul of 1.5 M 1-ethyl-3-[3-dimethylaminopropyl] carbodiimide were then added and the mixture was incubated for 1 hour at 23° C. RNA was isolated from this mixture by spin column chromatography through Sephadex G-50. The 5'-imidazolide of [5,-$^{32}$P]MDV-1 RNA (together with unconverted [5'-$^{32}$P]MDV-1 RNA) was collected in 100 ul of 100 mM NaCl, 1 mM EDTA, 10 mM Hepes, pH 7.5..1 M 2,2'-dithiobis(ethylamine)dihydrochloride (cystamine dihydrochloride), pH 7.7, was then added to a final concentration of 250 mM, and the solution was incubated for 1 hour at 50° C. The RNA was then isolated by spin column chromatography through Sephadex G-50 and precipitated with ethanol.

Conversion of 5'-cystamine-MDV-1 RNA to 5'-biotinylated Cystamine-MDV-1 RNA

The 5'-cystamine-[$^{32}$P]MDV-1 RNA (together with unconverted [$^{32}$P]MDV-1 RNA) was dissolved in 40 ul of 200 mM Hepes, pH 7.7, 1 mM EDTA, containing 360 ug N-hydroxysuccinimidobiotin, and incubated for 40 minutes at 23° C. Excess N-hydroxysuccinimidobiotin was removed by centrifugation, and the RNA was then precipitated with ethanol. The 5'-biotinylated MDV-1 RNA (I) (together with nonbiotinylated RNA) was further freed of excess N-hydroxysuccinimidobiotin by electrophoresis on a denaturing gel. The RNA in the $^{32}$P-labeled band was eluted from the gel and purified by several precipitations with ethanol.

Separation of 5'-biotinylated MDV-1 RNA from Nonbiotinylated MDV-1 RNA 50 to 200 ng of partially 5'-biotinylated [$^{32}$P]MDV-1 RNA was incubated with 2 to 10 ug avidin DN (a highly purified form of avidin purchased from Vector Laboratories, Burlingame, Calif., U.S.A.) for 45 minutes at 23° C. in 10 mM Hepes, pH 7.7, 1 mM EDTA. The 5'-biotinylated [$^{32}$P]MDV-1 RNA-avidin adduct (II) was separated from nonbiotinylated [$^{32}$P]RNAs and free avidin by electrophoresis on a denaturing gel. The 5'-biotinylated MDV-1 RNA-avidin adduct was then extracted from the gel and precipitated with ethanol.

Identification of the RNA-biotin-avidin Adduct (II) by its Formation of a Complex with Biotinylated Agarose The 5'-biotinylated [$^{32}$P]MDV-1 RNA-avidin adduct and the 5'-cystamine-[$^{32}$P]MDV-1 RNA were eluted from the gel and precipitated several times with ethanol. Each adduct was incubated with 50 ul biotinylated agarose for 15 minutes at 23° C. in 10 mM Hepes; pH 7.7, 1mM EDTA. The agarose was precipitated by centrifugation and washed twice with buffer. The fraction of each radioactive adduct that was precipitated by the biotinylated agarose was determined on a scintillation counter.

5'-thio-ethylamino-MDV-1 RNA

The [$^{32}$P]MDV-1 RNA-biotin-avidin adduct was converted to the 5'-thio-ethylamino-[$^{32}$P]MDV-1 RNA and a biotin-avidin by-product by reduction with dithiothreitol. 60 ng of 5'-biotinylated [$^{32}$P]MDV-1 RNA-avidin adduct were incubated for 1 hour at 23° C. in 30 ul of 100 mM dithiothreitol (DTT), 1 mM EDTA, 10 mM Hepes, pH 7.7, to cleave the disulfide bond of the spacer linker arm. 40 ul of biotinylated agarose were then added to the reaction mixture and incubated for 1 hour at 23° C. to bind the biotin-avidin by-product. The biotinylated agarose was removed from the solution by centrifugation.

95% of the radioactivity was recovered from the supernatant, confirming that the disulfide linker arm had been cleaved. In a control reaction, in which unreduced RNA-biotin-avidin adduct was incubated with biotinylated agarose, less than 10% of the radioactivity was found in the supernatant.

The cleaved RNA was recovered by precipitation with ethanol and analyzed by electrophoresis on a non-denaturing gel in the presence of 100 uM dithiothreitol (to prevent dimerization of the reduced RNA). The 5'-thio-ethylamino-MDV-1 RNA migrated through the gel at the same rate as a 5'-phosphorylated MDV-1 RNA control, while the unreduced adduct migrated at a slower rate. The 5'-biotinylated MDV-1 RNA-avidin adduct (II) and the 5'-thio-ethylamino-MDV-1 RNA were each tested to see whether they could serve as templates for the synthesis of MDV-1 RNA by Qβ replicase.

5 ng each of the modified [$^{32}$P]MDV-1 RNAs to be tested were incubated with 4.6 ug of Qβ replicase at 37° C. in 50 ul of 400 uM ATP, 400 uM CTP, 400 uM [alpha-$^{32}$P]GTP (500 mCi/mmol), 400 uM UTP, 12 mM $MgCl_2$, 84 mM Tris-HCl, pH 7.5. 2-ul samples were taken every minute between 1 and 15 minutes. Each sample was absorbed onto a numbered semicircle (23 mm diameter) of 3MM filter paper (Whatman) and immersed in a beaker containing ice-cold 300 mM phosphoric acid, 20 mM sodium pyrophosphate, 1 mM EDTA. The filter papers were washed six times with the same solution to elute the labeled precursors from the precipitated RNA trapped in the fibers. The filters were then washed once with ethanol, dried in air, and their radioactivity was determined in a scintillation counter. The results indicated that both of the 5'-modified RNAs served as templates for Qβ RNA replicase. The rate of RNA synthesis in each reaction was the same as the rate of synthesis seen in a control reaction initiated with 100 ng/ml unmodified MDV-1 RNA.

This example shows that neither the chemical procedures involved in linking biotin to MDV-1 RNA, nor the attachment of avidin to the 5'-terminal biotin group, interferes with enzymatic replication of the RNA sequence. The fact that the 5'-terminal biotin-avidin does not interfere with enzymatic replication of the RNA can be attributed to the site of attachment of the biotin and the length of the spacer arm, illustrated in the following figure:

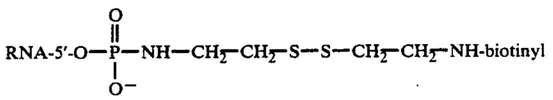

RNA synthesis initiates at the unmodified 3'-end of the template (A. K. Banerjee et al., J. Mol. Biol. 46, 445–455 (1969)), and the spacer arm must provide more than adequate space for termination of replication at the 5'-end of the template.

EXAMPLE II

Human gamma globulin (IgG) is isolated from serum of (A) a patient with recent exposure to Rubella and (B) a patient unexposed to Rubella and whose antiserum had previously tested negative for reaction with Rubella antigen. To tag the IgG in each sample with biotin, each sample is diluted to 4 mg protein/ml in borate buffered saline, pH 8.5. 50 microliters of biotinyl-N-hydroxysuccinimide ester dissolved in dimethylformamide (10 mg/ml) is added to each ml of the diluted samples. The reaction mixtures are stirred at room temperature for two hours and then dialyzed overnight against, per ml, 1 liter of phosphate buffered saline (PBS), pH 7.4 at 4° C. The resulting solution, which contains biotinylated IgG, is stored at 4° C. in the Presence of sodium azide.

Polystyrene microtiter plates, with wells coated with Rubella antigen in 0.1 M sodium carbonate buffer at pH 9.8, are incubated for 3 hours at room temperature with 50 ul aliquots, per well, of 1:10, 1:30, 1:100, 1:300, 1:1000 and 1:3000 dilutions of the biotinylated IgG-containing solutions prepared as described above. A plate with wells not coated with Rubella antigen is employed for control. The dilutions of IgG preparations were with 5% horse serum in PBS. After incubation with the dilutions of the biotinylated IgG preparations, the plates are washed 3 times with NaCl-Tween 20.

To each well of the microtiter plates is then added 50 ul of a solution in PBS of the MDV-1 biotin-avidin adduct (II) prepared as in Example I, at 1 to 10 ug/ml concentration, and the wells are then incubated with the solution for two hours at room temperature. Then the plates are washed 3 times with NaCl-Tween 20.

Then 0.1 M DTT in Tris buffer (pH 7.5) is added to all of the wells, and the resulting mixtures are incubated at room temperature for one hour.

Each well is then incubated with 4.6 ug of Qβ replicase at 37° C. in 50 ul of 400 uM ATP, 400 uM CTP, 400 uM [alpha-$^{32}$P]GTP (500 mCi/mmol), 400 uM UTP, 12 mM $MgCl_2$, 84 mM Tris-HCl, pH 7.5. 2 ul samples are taken every minute between 1 and 15 minutes. Each 2 ul sample is absorbed onto a numbered semicircle (23 mm diameter) of 3MM filter paper (Whatman) and immersed in a beaker containing ice-cold 300 mM phosphoric acid, 20 mM sodium pyrophosphate, 1 mM EDTA. The filter papers are washed 6 times with the same solution to elute the labeled precursors from the precipitated RNA trapped in the fibers. The filters are then washed once with ethanol and dried in air, and their radioactivity is determined in a scintillation counter. Radioactivity above background is indicative of the presence of anti-Rubella IgG in assayed serum.

EXAMPLE III

5'-biotin-hex-P-16-mer, consisting of biotin linked via a hexamethylene diamine linker to the 16-mer 5'-CACAATTCCACACAAC-3', with sequence complementary to that of a segment of M13mp8 DNA, is prepared in accordance with B. C. F. Chu and L. E. Orgel, DNA 4 327-331(1985). Also in accordance with this reference, nitrocellulose blots containing 10 ng, 1 ng, 0.1 ng, 0.01 ng and 0.001 ng of single stranded M13mp8 DNA are prepared, as are control blots containing no DNA.

The blots are cut and transferred to microtiter wells where they are reacted with a large excess of the MDV-1 biotin-avidin adduct prepared as in Example I (50 ul per well, with adduct concentration from about 1 to about 10 ug/ml in PBS). Each of the blots is then washed thoroughly with NaCl-Tween 20 and then transferred to fresh microtiter plates, where they are first incubated with 0.1 M DTT in Tris buffer (pH 7.5) for 1 hour and then incubated with 50 ul (per well) of the Qβ replicase-containing solution described in Example II above. Two ul samples are taken every 90 seconds between 1 and 30 minutes and blotted onto filter papers as described in Example II, for measurement of radioactivity in a scintillation counter Radioactivity above background is indicative of M13mp8 DNA on the assayed blots.

EXAMPLE IV

This Example is performed in the same way as Example III, except that the blots are not incubated with DTT and, consequently, the disulfide bond joining the MDV-1 RNA to the biotin-avidin is not cleaved and the MDV-1 RNA remains bound to the 16-mer probe (and M13mp8 analyte). However, the blots are incubated with the Qβ replicase solution and samples are taken and radioactivity measured as described in Example III.

EXAMPLE V

This Example is carried out in the same way as Example III, except that, in place of the incubation with DTT, the Tris buffer (pH 7.5) is added to the wells and the microtiter plate is heated to 80° C. for 10 minutes to release the probe joined to MDV-1 RNA reporter group from the nitrocellulose-blotted M13mp8 analyte. After cooling to room temperature, the samples are incubated with the Qβ replicase solution, and otherwise treated as in Example IV.

EXAMPLE VI

The 16-mer oligonucleotide probe described in Examples III-V is biotinylated in a photochemical reaction with photobiotin acetate as described by Forster et al., Nucleic Acids Res. 3, 745-761 (1985). The biotinylated oligonucleotide is separated from the starting material by high performance liquid chromatography with RPC-5. The biotinylated 16-mer is then employed to detect M13mp8 DNA following the procedure of Example III.

EXAMPLE VII

A 300-base segment of M13mp8 DNA is obtained from phage and chemically labeled with biotin, using photobiotin acetate according to the procedure of Forster et al., supra. The dot-blot hybridization protocol described by Forster et al., supra, is followed. Then the blots are incubated with MDV-1 RNA biotin-avidin reporter adduct as described in Example III, and the remainder of the procedure of Example III is followed to detect M13mp8 DNA.

EXAMPLE VIII

Uridine residues, biotinylated through a spacer arm to the carbon-5 position, are introduced into the oligonucleotide described in Example III by the nick-translation procedure described by Langer et al., supra and Leary et al., supra. Then, with the resulting biotinylated 16-mer, following the procedure of Example III with MDV-1 biotin-avidin reporter adduct, an assay for blotted M13mp8 DNA is carried out.

EXAMPLE IX

This Example shows the use of a recombinant RNA as a "self-reporting" affinity molecule for a nucleic acid analyte, i.e., an affinity molecule which is also a replicative RNA for its own detection in an assay system according to the invention.

The Example also shows biotinylation of replicated reporter group RNA to provide detectability.

Following the procedure of Miele et al. (1983), supra, and Kramer et al., U.S. patent application Ser. No. 614,350, supra, a recombinant RNA is prepared which consists of MDV-1 RNA with the 30-mer oligoribonucleotide 5'-AGUCAGGCACCGUGUAUGAAAUCUAACAAU-3' inserted between the G at position 63 and the U at position 64 of the MDV-1 sequence. The 30-mer has a sequence complementary to that of a segment of plasmid pBR322 (see positions 71 to 100 in the pBR322 sequence provided in Appendix B of Maniatis et al., supra).

Following the procedure of Matthews et al., Anal. Biochem. 151, 205–209 (1985), with nitrocellulose support, the recombinant RNA is hybridized to blots which include from 2 ng to 0.01 pg of pBR322 DNA. 5 ng of recombinant RNA is employed in each hybridization. The recombinant RNA is denatured by boiling and subsequently added to hybridization solution (45% formamide, 20 mM Na phosphate, 5 ×SSC, 0.1% Ficoll 400, 0.1% bovine serum albumin, 0.1% polyvinyl-pyrrolidone, 250 mg/ml denatured salmon sperm DNA, pH 6.4). The hybridization is then carried out for 12 hours at 42° C.

Following the hybridization and post-hybridization washes, individual circles corresponding to the samples are cut from the blots and, treated separately, immersed in Tris buffer (pH 7.5) and heated to 100° C. for 10 minutes to separate hybridized recombinant RNA into solution. After the solution in the wells is cooled to room temperature, 50 ul of a solution of Qβ replicase, the same as that described in Example II, except that the radioactively labeled GTP is replaced with non-radioactively labeled GTP and the unlabeled UTP is replaced with biotinylated UTP (Biotin-11-UTP purchased from Bethesda Research Laboratories, Gaithersburg, Md., U.S.A.; this is UTP with biotin joined to carbon-5 of the uracil moiety through an 11-atom spacer arm, see Langer et al., supra; Ward et al, European Publication No. 0 063 879), is added to each well and the plate is incubated at 37° C. Every 90 seconds for 30 minutes, using a 96-finger aliquotter, 2 ul of solution from each well is blotted onto a nitrocellulose filter (with an area corresponding to each well marked on it), and each filter is developed, following the procedure of Matthews et al., with streptavidin-peroxidase complex with a chemiluminescent reagent (1.25 mM luminol, 2.7 mM $H_2O_2$, 0.1 M Tris buffer, pH 8.6, with 0.136 mM p-iodophenol or 0.68 uM p-hydroxycinnamic acid as enhancer). The light emitted from the spots on the filters is then read using a luminescent microtiter plate reader. Emission above background (i.e., emission from spots associated with the procedure carried out with no pBR322 DNA analyte) indicates the presence of pBR322 analyte in the assayed solutions.

EXAMPLE X

An adduct of the 16-mer described in Example II with the group $—O—PO_2—NH—(CH_2)_2—S—S—(CH_2)_2NH_2$ bound to the 5′-carbon of the 5′-nucleotide is prepared by the procedure of Chu and Orgel, DNA 4, 327–331 (1985), except that cystamine is used in place of hexamethylene diamine. From this disulfide adduct, the (2-thioethyl)amino adduct, with $—O—PO_2—NH(CH_2)_2SH$ bound to the 5′-carbon of the 5′-nucleotide, is prepared by incubation with 0.1 M DTT for 1 hour at room temperature. The thio adduct is then isolated from unreduced disulphide adduct by high performance liquid chromatography with RPC-5 in the presence of 1 mM DTT.

The MDV-1 RNA adduct with $—O—PO_2—NH(CH_2)_2SS(CH_2)NH_2$ bound to the 5′-carbon of the 5′-nucleotide is prepared as described in Example I. The ethanol precipitated disulphide adduct-containing product from that procedure is then dissolved in 0.1 M DTT, and the resulting solution is incubated for 1 hour at room temperature to provide the corresponding thio adduct.

50 ul of the 0.1 M DTT solution, containing about 50 ng of the thio adduct of MDV-1 RNA, is combined with a 10-fold molar excess of thio adduct of the 16-mer (i.e., an amount of solution from the HPLC purification that contains about 30 ng of the thio adduct). $O_2$ is bubbled through the resulting solution for 15 minutes, and the ensuing reaction of the two thio adducts is allowed to proceed overnight at room temperature. Employing gel electrophoresis, the MDV-1 RNA with 16-mer joined through the disulphide-containing moiety is separated from other MDV-1 RNA adducts and unreacted 16-mer adduct.

The MDV-1 RNA adduct with 16-mer joined through the disulphide containing moiety is then employed, in place of MDV-1 RNA biotin-avidin, to detect M13mp8 DNA following the procedure of Example III.

EXAMPLE XI

This example describes the detection of a specific antigen on cell surfaces employing a reporter system according to the invention. The procedures described here are based in part on the teaching of Horan-Hand et al., Cancer Research 43, 728–735 (1983).

The procedures are illustrated with a murine monoclonal IgG antibody prepared by standard techniques against the antigen being assayed. The skilled will understand that other types of antibodies specific for the antigen analyte could be employed as well.

(a) Procedure employing monolayer cultured cells:

Cells to be tested are seeded in flat, 96-well flat bottom tissue culture plates with appropriate growth medium and are incubated at 37° C. for 24 hours. The growth medium is then replaced with growth medium containing 10% (w/v) bovine serum albumin (BSA). After incubation for 60 minutes, the 10% BSA containing medium is removed and the wells are washed with wash medium (RPMI 1640 medium supplemented with 1% (w/v) BSA). The wash medium is then removed and replaced with, per well, 50 ul of monoclonal antibody, at 0.1 mg/ml in PBS, against the antigen analyte and the mixture is incubated at 4° C. for 2 hours. After the incubation, unbound antibody is removed by aspiration of antibody solution and followed by washing with wash medium. Following the washing, to each well is added 50 ul of a 1:1000 dilution with wash medium of biotinylated rabbit anti-mouse IgG, as purchased from Vector Laboratories, Burlingame, Calif., U.S.A., and the solution is incubated in the wells at 4° C. for two hours. The anti-IgG antibody solution is then aspirated from the wells, and they are then washed again with wash medium. Then to each well is added 50 ul of a solution in PBS of the MDV-1 RNA biotin-avidin adduct of Example I, at 1 to 10 ug/ml, and the solution is incubated in the wells at 4° C. for 2 hours. This solution is then aspirated from the wells, and they are washed three times with wash medium. 50 ul of 0.1 M DTT in Tris-HCl buffer (pH 7.5) is then added to each well, and incubation for 1 hour at room temperature is carried out. Then, using a 96-finger aliquotter, the supernatants from each well are removed to a well in a fresh microtiter plate and, following the procedure of Example II, the solutions are combined with a Qβ replicase solution and assayed for replicated MDV-1 RNA.

(b) Procedure employing cells in suspension:

Cells in suspension can be tested for a particular antigen by the procedure used for monolayer cultivated cells, with the following modifications:

If cells are not obtained in the form of a single-cell suspension (e.g., lymphocytes from serum), they are treated appropriately to prepare such a suspension. For example, cells from a tissue culture can be trypsinized by standard techniques to be loosened from surfaces of the culture vessel and then the resulting solution can be pipetted from the culture vessel into an appropriate medium.

Cells in a single-cell suspension are then divided into wells of a microtiter plate and washed twice with RPMI 1640 medium without added BSA. The cells, in suspension, are then incubated for 2 hours at 4° C. with, per well, 50 ul of 0.1 mg/ml in PBS of antibody against the antigen of interest.

The remainder of the procedure is the same as that for monolayer cultured cells.

Washings of cells in suspension culture are carried out by centrifugation to produce a pellet, aspiration of medium, and then a cycle (for each wash) of resuspension of pellet in fresh medium (wash medium), re-pelleting, and aspiration of medium.

For procedures of this example, cells known to be free of antigen analyte may be employed as controls.

The procedures described above in this example involve binding of a biotinylated second antibody to the primary antibody, that binds to antigen analyte. Alternatively, the primary antibody itself can be biotinylated, provided the biotinylation does not eliminate its capacity to bind specifically to antigen analyte, and the second antibody binding step can then be avoided. Biotinylation of antibody can be carried out by reaction of antibody directly with N-hydroxysuccinimidobiotin, following the procedure of Imam et al., Cancer Research 45, 263–271 (1985).

EXAMPLE XII

This example describes a use of assays according to the invention to detect protein, from a cell lysate, serum or other solution. The procedure described is a type of "Westerm blot" procedure.

If cells are involved, a cell lysate is prepared by a standard procedure, such as solubilizing with a 100° C. solution containing 2% sodium dodecyl sulfate, 2% 2-mercaptoethanol, and 10% glycerol in Tris-HCl buffer, pH 6.8.

The lysate (or serum or other solution) is then subjected to polyacrylamide gel electrophoresis in duplicate, with the protein to be detected run as a marker in a neighboring lane. Employing a standard blotting apparatus (e.g., Trans-Blot apparatus, Bio-Rad Laboratories, Richmond, Calif. U.S.A.), the proteins are transferred from the gel to nitrocellulose sheets. One of the experimental gel lanes and the marker gel lane are stained with Coomassie Blue. The zone that would contain the protein analyte, if present in the sample, is then cut from the experimental lane. The zone of the nitrocellulose paper corresponding to the gel zone that might contain analyte is cut from the paper, and soaked with 3% (w/v) BSA in distilled water for 1 hour at 37° C. to saturate all non-specific protein binding sites.

Employing a biotinylated antibody against the protein as affinity molecule, the procedure of the following example is employed to test whether the protein analyte is on the nitrocellulose strip.

EXAMPLE XIII

This example illustrates the detection of cell surface glycoproteins with an assay according to the instant invention. The procedure of this example is a variation of that of Gordon and Pena, Biochem. J. 208, 351–358 (1982), who used peanut agglutinin and castor bean agglutinin I to detect specific cell-surface glycoproteins on neuraminidase-treated, cultured, normal and abnormal human skin fibroblasts.

Cells are plated on culture dishes at a density of about $2\times10^4$ cells/cm$^2$. After 24 hours, the cells are washed and solubilized with a 100° C. solution of 2% (w/v) sodium dodecylsulfate, 2% (w/v) 2-mercaptoethanol, 10% (v/v) glycerol, 0.01% bromophenol blue in 0.125 M Tris-HCl buffer, pH 6.8. The lysate is then subjected to SDS-polyacrylamide gel electrophoresis, and proteins are transferred to nitrocellulose sheets employing a Trans-Blot apparatus (Bio-Rad Laboratories). The nitrocellulose sheet is cut into strips of about 5 cm$^2$ area. The resulting nitrocellulose strips are soaked in 3% (w/v) BSA in water for 1 hour at 37° C. to saturate all non-specific protein-binding sites. The strips are then rinsed with HBS solution (137 mM NaCl, 2.7 mM KCl, 0.9 mM $CaCl_2$, 0.5 mM $MgCl_2$, 30 mM Hepes, pH 7.4) and are then incubated for 1 hour at room temperature, with 1.5 ml of solution of the biotinylated lectin, appropriate for the carbohydrate moiety of interest on the glycoproteins of the lysate, at 10 mg/ml in HBS solution containing 3% BSA. Biotinylated lectins are commercially available, as from, e.g., Vector Laboratories, Burlingame, California. The strips are then thoroughly washed by soaking 4 times for 30 minutes with HBS solution, and are then incubated for 1 hour at room temperature with 0.5 ml of the MDV-1 RNA biotin-avidin adduct of Example I, at about 5 ug/ml in PBS. After the incubation with avidin-biotin MDV-1 RNA adduct, excess adduct is washed away with 3 washes with HBS. The strips are then incubated with 0.5 ml of 0.1 M DTT in Tris-HCl (pH 7.5) for 1 hour, and the resulting solutions are assayed, with Q$\beta$ replicase catalyzed RNA replication, for MDV-1 RNA by the procedure of Example II.

EXAMPLE XIV

Nucleic acid from biological specimens (e.g., cell cultures, tissues, blood, other body fluids, food materials and the like) is assayed for analyte segments or analyte molecules by an assay according to this invention by first disrupting the specimen by standard techniques to expose nucleic acid (e.g., incubation of about 5 ul of the specimen at 45° C. for 20 minutes with between about 5 ul to about 1 ml of 30 mM Tris-HCl, 2 mM EDTA, 3% Triton X-100, 300 ug/ml proteinase K, pH 7.5), then blotting the resulting solution onto a solid support (e.g., nitrocellulose) to fix the nucleic acid, and then carrying out procedures, such as those described in Examples III-X, to detect the nucleic acid analyte.

Controls in such assays can be biological specimens similar to those being assayed but known to be free of analyte.

For quantitative estimates of the amount of analyte in a specimen, controls to which known quantities of analyte have been added can be employed, and then the amount of analyte in a specimen estimated by comparing the rate of replication of replicative RNA associated with test specimen with the rates associated with the controls.

EXAMPLE XV

The procedure of Example IX is followed, except that only unmodified ribonucleoside triphosphates are used in the replication reaction and replicated RNA is detected as follows:

The aliquots (of equal volume) of replication reaction solutions are transferred with the 96-finger aliquotter to sheets of diethylaminoethyl cellulose paper.

The sheets are then washed at room temperature in a solution of 200 mM NaCl, 300 mM ammonium acetate, pH 6.0, to remove ribonucleotides not incorporated into RNA.

The sheets are then stained with 0.3 ug/ml ethidium bromide. See Sharp et al., Biochemistry 12, 3055–3063 (1973) and Bailey and Davidson, Anal. Biochem. 70, 75–85 (1976).

Finally the fluorescence from individual blots is measured by any of several known techniques. Fluorescence intensity from a stained blot above that from control blots indicates the presence of analyte (i.e., pBR322) in the sample blot corresponding to the stained blot.

Other staining materials, can be employed in place of ethidium bromide. These include methylene blue (Dingman and Peacock (1968), supra); silver stain (Sammons (1981), supra; Igloi (1983), supra); or phycobiliprotein-Qβ replicase conjugate (Oi et al. (1982), supra; Stryer et al., supra).

Further, rather than measuring fluorescence, color of the blots due to staining of RNA can be measured.

EXAMPLE XVI

A culture of E. coli K-12/C600 is transformed with pBR322 and cultured in the presence of tetracycline to $10^8$ cells/ml. 0.1 ml of culture is combined with each of 0.1 ml, 1 ml, 10 ml, 100 ml and 1,000 ml of a solution of 30 mM Tris-HCl, 2mM EDTA, 3% Triton X-100, 300 ug/ml proteinase K, pH 7.5, and the resulting solutions are heated at 45° C. for 20 minutes.

A control solution is prepared by culturing without tetracycline E. coli K-12/C600, not transformed with pBR322, to $10^8$ cells/ml and then combining 0.1 ml of the culture with 0.1 ml of the above-specified proteinase K solution and heating the resulting solution for 20 minutes at 45° C.

Then 3 ul of each of 3 samples of each of the 5 test solutions and the control solution are dot-blotted onto a nitrocellulose support, on 18 of the 96 spaces in a standard 96-well arrangement. The support is then placed on top of a paper towel saturated with 400 mM NaOH to denature the DNA, and is then placed in contact successively with a paper towel saturated with (a) 400 mM Tris-HCl, pH 7.0, (b) 20 X SSC; and (c) 10 X SSC. Finally, the nitrocellulose sheet is baked at 80° C. for 90 minutes.

The 30-mer of Example IX is joined, following the procedures of Examples I and X, to MDV-1 (+) RNA by a moiety of formula $—O(-PO_2)NH(CH_2)_2SS(CH_2)_2NH(PO_2)O—$, where the phosphoramidate groups are bonded to the 5′-carbons of the 5′-nucleotides of 30-mer affinity molecule and replicative RNA.

Following a standard procedure, the sheet is prehybridized, then hybridized with the resulting affinity molecule —MDV-1 RNA hybrid, at 3 ug/ml in hybridization solution, and then post-hybridization washed to remove unhybridized affinity molecule —MDV-1 RNA hybrid.

Then the nitrocellulose sheet is placed on top of a sheet of ECTEOLA paper (Sarris et al., (1982), supra) that in turn is on top of dry paper towels. A wet sponge saturated with 0.1 M DTT in 0.05 M Tris-HCl (pH 7.5) is placed on top of the nitrocellulose sheet. Along with capillary transfer of DTT solution to the paper towels, replicative RNA, released by reduction of the disulfide of the hybrid, is replica transferred to the ECTEOLA paper, where it is affixed by the positive charge.

The ECTEOLA paper is then incubated with a solution of 100 ug/ml BSA to block protein binding sites.

The paper is then incubated for 15 minutes with the Qβ replicase solution described in Example II. Following the 15 minute incubation, the paper is washed with a solution of 200 mM NaCl, 5 mM sodium phosphate, pH 6.5 to remove unincorporated ribonucleotides. The radioactivity of each blot on the ECTEOLA paper is then determined using, e.g., a 96-position β-emission scanner/digitizer (Goulianos et al., Anal. Biochem 103, 64–69 (1980).

Alternatively, the replication could have been carried out with only non-radioactive ribonucleoside triphosphates and the amount of RNA determined by its intrinsic UV absorbance (e.g., as by the contact photoprinting method of Kutateladze et al. (1979), supra) or, directly on the ECTEOLA paper, by one of the staining techniques described in Example XV.

The presence of pBR322 in the solution being assayed is indicated by a signal, above background signal (from control solutions), from the corresponding RNA replica blots on the ECTEOLA paper.

EXAMPLE XVII

Cultures of E. coli K-12/C600, transformed and not transformed with pBR322, are prepared as in Example XVI.

Then 3 ul each of 3 samples of each of undiluted control, undiluted pBR322-transformed culture, 1:10 diluted pBR322-transformed culture, 1:100 diluted pBR322-transformed culture, 1:1000 diluted pBR322-transformed culture and 1:10000 diluted pBR322-transformed culture (all dilutions with cell free culture medium) are added to polypropylene microcentrifuge tubes. To each well is added 5 ul of a solution of 30 mM Tris-HCl, 2 mM EDTA, 2% Triton X-100, 300 ug/ml proteinase K, pH 7.5. The plate is then incubated for 20 minutes at 45° C. At the end of the 20 minutes, the temperature is raised to 100° C. and incubation continues for 5 additional minutes. After the plate has cooled at room temperature, 8 ul of an aqueous salt solution/-phenol suspension of the affinity molecule-MDV-1 RNA hybrid of Example XVI, at 5 ug/ml, is added to each well and hybridization is carried out for 5 minutes, following Kohne et al. (1977), supra.

The water-phenol mixture from each well is then subjected to agarose gel electrophoresis to separate pBR322 (both hybridized and not hybridized with affinity molecule-MDV-1 RNA) from the much smaller affinity molecule-MDV-1 RNA. The gels are soaked in 0.1 M DTT, 0.05 M Tris-HCl, pH 7.5 to release replicative RNA by cleavage of the disulfide between affinity molecule and the RNA.

The replicative RNA is then transferred to ECTEOLA paper by electroblotting (Stellwag and Dahlberg, Nucl. Acids Res. 8, 299–317 (1980).

Finally, the procedures of Example XVI, after the step at which replicative RNA is replica-blotted in ECTEOLA paper, are followed to replicate replicative RNA, detect the replicated RNA, and ascertain whether pBR322 was in the samples being assayed.

The present invention involves a bioassay system significantly improved over prior art systems because of the sensitivity that can be achieved by the use of the reporter system based on replication of RNAs by RNA-dependent RNA polymerases. The sensitivity of assays employing these reporter systems should be limited only by background due to non-specific adsorption of affinity molecule and replicative RNA. Otherwise, the sensitivity of such assays should be close to the theoretical limit of one molecule of analyte per sample.

While the invention has been described with some specificity, modifications apparent to those with ordinary skill in the art may be made without departing from the scope of the invention.

Various features of the invention are set forth in the following claims.

What is claimed is:

1. A method of determining the presence of a biopolymer analyte in a sample, which method comprises (i) exposing the sample to an affinity molecule for said analyte under conditions whereby binding occurs between the affinity molecule and the analyte;

(ii) if said affinity molecule is not itself a replicative RNA, which is a template for replication in vitro by $Q\beta$ replicase, joining, either before or after step (i), a replicative RNA, which is a template for replication in vitro by $Q\beta$ replicase, to the affinity molecule employed in step (i);

(iii) employing $Q\beta$ replicase to catalyze replication of replicative RNA, which (a) is a template for replication in vitro by $Q\beta$ replicase and (b) or had been joined to affinity molecule bound to analyte or is affinity molecule that had been bound to analyte; and (iv) detecting RNA made by the reaction of step(iii).

2. A method according to claim 1 wherein the analyte is a nucleic acid, the affinity molecule is a replicative RNA which (a) is a template for replication in vitro by $Q\beta$ replicase and (b) includes a segment with a sequence of about 20-to about 4000 bases complementary to the sequence of a segment of the analyte, and the replication of said replicative RNA is after dissociation thereof from analyte.

3. A method according to claim 1 wherein the joining of replicative RNA, which is a template for replication in vitro by $Q\beta$ replicase, to affinity molecule is effected through a first linking moiety, joined to said replicative RNA without eliminating the replicability thereof by $Q\beta$ replicase, and a second linking moiety, joined to the affinity molecule without eliminating the specificity of binding between affinity molecule and analyte, said first and second linking moieties either being covalently joined to each other or being a specific binding pair.

4. A method according to claim 1 wherein the joining of replicative RNA, which is a template for replication in vitro by $Q\beta$ replicase, to affinity molecule is effected by hybridization of said replicative RNA to a segment of nucleic acid at least 10 bases in length joined to or included in affinity molecule.

5. A method according to claim 2 wherein the replication of replicative RNA is carried out with a radioactively labeled ribonucleoside-5'-triphosphate and the resulting replicated RNA is radioactively labeled.

6. A method according to claim 3 wherein the replication of replicative RNA is carried out with a radioactively labeled ribonucleoside-5'-triphosphate and the resulting replicated RNA is radioactively labeled.

7. A method according to claim 6 wherein, prior to exposing the affinity molecule to the sample, the first linking moiety and second linking moiety are covalently joined to each other by a disulphide moiety.

8. A method according to claim 7 wherein the first linking moiety is of formula $—O—PO_2\text{-}NH\text{-}(CH_2)_n—S—$, wherein the phosphoramidate moiety is bonded to the 5'-carbon of the 5'-nucleotide of the replicative RNA, which is a template for replication in vitro by $Q\beta$ replicase, and n is 2 to 8, and the second linking moiety is of formula $—O—PO_2—NH—CH_2)_m—S—$, wherein the phosphoramidate moiety is bonded to the 5'-carbon of the 5'-nucleotide of a nucleic acid affinity molecule and m is the same as or different from n and is 2 to 8.

9. A method according to claim 6 wherein the affinity molecule is a nucleic acid with a segment of at least 1 purine residue, which segment is at the 3'-terminus of the affinity molecule and outside the analyte-binding segment of the affinity molecule, said 3'-terminus of the affinity molecule bonded through a phosphodiester to the 5'-carbon of the 5'-nucleotide of the replicative RNA, which is a template for replication in vitro by $Q\beta$ replicase.

10. A method according to claim 7 wherein affinity molecule and replicative RNA, which is a template for replication in vitro by $Q\beta$ replicase, are combined in a smart probe.

11. A method according to claim 6 wherein the first and second linking moieties are a specific binding pair.

12. A method according to claim 11 wherein one of the first and second linking moieties is biotinyl and the other is avidin joined to affinity molecule or replicative RNA, which is a template for replication in vitro by $Q\beta$ replicase, through complexing to biotinyl.

13. A method according to claim 12 wherein a biotinyl moiety is linked to the 5'-nucleotide of the replicative RNA, which is a template for replication in vitro by $Q\beta$ replicase, by a spacer arm of formula $—O—OP_2—NH—(CH_2)_p(SS)_q(CH_2)_rNH—$, wherein the phosphoramidate moiety is bonded to the 5'-carbon of the 5'-nucleotide, wherein p and r are the same or different and are each 2 to 8, and wherein q is 0 or 1.

14. A method according to claim 13 wherein the affinity molecule is a biotinylated antibody and avidin is complexed to the biotinyl joined to replicative RNA, which is a template for replication in vitro by $Q\beta$ replicase.

15. A method according to claim 13 wherein the affinity molecule is a biotinylated lectin and avidin is complexed to the biotinyl joined to replicative RNA, which is a template for replication in vitro by $Q\beta$ replicase.

16. A method according to claim 13 wherein the affinity molecule is a nucleic acid biotinylated photochemically with photobiotin, enzymatically with dUTP or UTP that is linked to biotinyl through C-5 of the uracil moiety or dATP that is linked to biotinyl through C-6 or C-8 of the adenine moiety, or chemically at the 5'-carbon of the 5'-nucleotide through a spacer arm of formula $—O—PO_2—NH—(CH_2)_s(SS)_t(CH_2)_uNH—$, wherein the phosphocamidate moiety is bonded to the 5'-carbon of the 5'-nucleotide, wherein s and u are the same or different and are each 2 to 8, and wherein t is 0 to 1; and wherein avidin is complexed to biotinyl joined to replicative RNA, which is a template for replication in vitro by Qβ replicase.

17. A method according to claim 16 the affinity molecule is biotinylated at the 5′-carbon of the 5′-nucleotide.

18. A method according to claim 7 wherein, after binding of affinity molecule, joined to replicative RNA, which is a template for replication in vitro by Qβ replicase, to analyte, and prior to replication of said replicative RNA, said replicative RNA is severed from affinity molecule by reduction of the disulfide covalently joining the first and second linking moieties.

19. A method according to claim 8 wherein, after binding of affinity molecule, joined to replicative RNA, which is a template for replication in vitro by Qβ replicase, to analyte and prior to replication of said replicative RNA, said replicative RNA is severed from affinity molecule by reduction of the disulfide covalently joining the first and second linking moieties.

20. A method according to claim 9 wherein, after binding of affinity molecule, joined to replicative RNA, which is a template for replication in vitro by Qβ replicase, to analyte and prior to replication of said replicative RNA, said replicative RNA is severed from affinity molecule by acid depurination followed by β-elimination to sever the phosphodiester bond.

21. A method according to claim 10 wherein, after binding of affinity molecule, joined to replicative RNA, which is a template for replication in vitro by Qβ replicase, to analyte and prior to replication of said replicative RNA, said replicative RNA is severed from affinity molecule by reducing of the disulfide covalently joining the first and second linking moieties.

22. A method according to claim 13 wherein q in the spacer group is 1; and wherein, after binding of affinity molecule, joined to replicative RNA, which is a template for replication in vitro by Qβ replicase, to analyte and prior to replication of said replicative RNA, said replicative RNA is severed from affinity molecule by reduction of the disulfide of the spacer arm joining said replicative RNA to biotinyl.

23. A method according to claim 14 wherein q in the spacer group is 1; and wherein, after binding of affinity molecule, joined to replicative RNA, which is a template for replication in vitro by Qβ replicase, to analyte and prior to replication of said replicative RNA, said replicative RNA is severed from affinity molecule by reduction of the disulfide of the spacer arm joining said replicative RNA to biotinyl.

24. A method according to claim 15 wherein q in the spacer group is 1; and wherein, after binding of affinity molecule, joined to replicative RNA, which is a template for replication in vitro by Qβ replicase, to analyte and prior to replication of said replicative RNA, said replicative RNA is severed from affinity molecule by reduction of the disulfide of the spacer arm joining said replicative RNA to biotinyl.

25. A method according to claim 17 wherein q in the spacer group is 1; and wherein, after binding of affinity molecule, joined to replicative RNA, which is a template for replication in vitro by Qβ replicase, to analyte and prior to replication of said replicative RNA, said replicative RNA is severed from affinity molecule by reduction of the disulfide of the spacer arm joining said replicative RNA to biotinyl.

26. A method according to claim 4 wherein the affinity molecule is a nucleic acid.

27. An affinity molecule-replicative RNA hybrid wherein the affinity molecule is joined to a replicative RNA, which is a template for replication in vitro by Qβ replicase, through a first linking moiety, joined to said replicative RNA without eliminating the replicability thereof by Qβ replicase, and a second linking moiety, joined to the affinity molecule without eliminating the specificity of binding between affinity molecule and its analyte, said first and second linking moieties being covalently joined to each other or being a specific binding pair.

28. An affinity molecule-replicative RNA hybrid, in accordance with claim 27, wherein the second linking moiety and first linking moiety are covalently joined to the affinity molecule and the replicative RNA, respectively, and are covalently joined to each other by a disulfide moiety.

29. An affinity molecule-replicative RNA hybrid, in accordance with claim 28, wherein the affinity molecule is a nucleic acid, the first linking moiety is of formula $-O-PO_2-NH-(CH_2)_n-S-$, wherein the phosphoramidate moiety is bonded to the 5′-carbon of the 5′-nucleotide of the replicative RNA and n is 2 to 8, and the second linking moiety is of formula $-O-PO_2-NH-(CH_2)_m-S-$, wherein the phosphoramidate moiety is bonded to the 5′-carbon of the 5′-nucleotide of the affinity molecule, and m is the same as or different from n and is 2 to 8.

30. An affinity molecule-replicative RNA hybrid, in accordance with claim 27, wherein the affinity molecule is a nucleic acid with a segment of at least one purine residue which is at the 3′-terminus of the affinity molecule and outside the segment of affinity molecule with sequence complementary to that of target segment of analyte, said 3′-terminus of the affinity molecule bonded through a phosphodiester to the 5′-carbon of the 5′-nucleotide of the replicative RNA.

31. An affinity molecule-replicative RNA hybrid, in accordance with claim 27, wherein the first and second linking moieties are a specific binding pair.

32. An affinity molecule-replicative RNA hybrid, in accordance with claim 31, wherein one of the linking moieties is biotinyl and the other is avidin, joined to the affinity molecule or the replicative RNA through complexing to biotinyl.

33. An affinity molecule-replicative RNA hybrid, in accordance with claim 32, wherein a biotinyl moiety is linked to the 5′-nucleotide of the replicative RNA by a spacer arm of formula $-O-PO_2-NH-(CH_2)_p(SS)_q(CH_2)_rNH-$, wherein the phosphoramidate moiety is bonded to the 5′-carbon of the 5′-nucleotide, wherein p and r are the same or different and are each 2 to 8, and wherein q is 0 or 1.

34. An affinity molecule-replicative RNA hybrid, in accordance with claim 33, wherein the affinity molecule is a biotinylated antibody.

35. An affinity molecule-replicative RNA hybrid, in accordance with claim 33, wherein the affinity molecule is a biotinylated lectin.

36. An affinity molecule-replicative RNA hybrid, in accordance with claim 33, wherein the affinity molecule is a nucleic acid biotinylated photochemically with photobiotin, enzymatically with dUTP or UTP, that is linked to biotinyl through C-5 of the uracil moiety, or dATP, that is linked to biotinyl through C-6 or C-8 of the adenine moiety, or chemically at the 5′-carbon of the 5′-nucleotide through a spacer arm of formula $-O-PO_2-NH-(CH_2)_s(SS)_t(CH_2)_uNH-$, wherein the phosphoramidate moiety is bonded to the 5'-carbon of the 5'-nucleotide, wherein s and u are the same or different and are each 2 to 8, and wherein t is 0 or 1.

37. An affinity molecule-replicative RNA hybrid, in accordance with claim 36, wherein the affinity molecule is biotinylated at the 5'-carbon of the 5'-nucleotide.

38. A replicative RNA, which is a template for replication in vitro by Qβ replicase, joined to a linking moiety, without eliminating the replicability in vitro of the replicative RNA by Qβ replicase, said linking moiety being capable of effecting a linkage between the replicative RNA and an affinity molecule through covalent linkage to, or being one member of a specific binding pair with, a linking moiety which is joined to the affinity molecule.

39. A replicative RNA in accordance with claim 38 wherein the linking moiety to which the replicative RNA is joined is sulfur, biotinyl, or avidin which is joined through a complex with biotinyl which, in turn, is joined to the replicative RNA.

40. A replicative RNA in accordance with claim 39 wherein the linking moiety is biotinyl or avidin, and, with either, biotinyl is linked to the 5'-nucleotide of the replicative RNA by a spacer group of formula $—O—PO_2—NH—(CH_2)_p(SS)_q(CH_2)_rNH—$, wherein the phosphoramidate moiety is bonded to the 5'-carbon of the 5'-nucleotide, wherein p and r are the same or different and are each 2 to 8, and wherein q is 0 or 1.

41. A replicative RNA in accordance with claim 39 wherein the linking moiety is sulfur and is joined to the 5'-nucleotide of replicative RNA by a spacer group of formula $—O(PO_2)NH(CH_2)_p—$, wherein the phosphoramidate group is joined to the 5'-carbon of the 5'-nucleotide and wherein p is 2 to 8.

42. A smart probe comprising a replicative RNA, which is a template for replication in vitro by Qβ replicase, covalently joined to a nuclei acid affinity molecule.

43. A smart probe according to claim 42 wherein the 5'-carbon of the 5'-nucleotide of the replicative RNA and the 5'-carbon of the 5'-nucleotide of the affinity molecule are joined by a moiety of formula $—O(PO_2)NH(CH_2)_y(SS)(CH_2)_zNH(PO_2)O—$, wherein y and z are the same or different and are each from 2 to 8.

44. A smart probe according to claim 43 wherein the affinity molecule has both a 5'-clamp segment and a 3'-clamp segment.

45. A smart probe according to claim 43 wherein the replicative RNA is a recombinant replicative RNA with a segment with a sequence complementary to that of a segment at the 3'-end of the affinity molecule.

* * * * *

UNITED STATES PATENT AND TRADEMARK OFFICE

CERTIFICATE OF CORRECTION

PATENT NO. : 4,957,858

DATED : September 18, 1990

INVENTOR(S) : Chu, et al.

It is certified that error appears in the above-identified patent and that said Letters Patent is hereby corrected as shown below:

TITLE PAGE: Under "Filed:", change "April 16, 1988" to --April 16, 1986--.

Other Publications, Page 1: Under "Cosstick et al.", change "Oligodeoxynucloetides" to --Oligodeoxynucleotides--.

Other Publications, Page 1: Under "Dreyer, et al.", change "Single-s-tranded" to --Single-stranded--.

Other Publications, Page 1: Under "Foster et al.", change "Foster" to --Forster--.

Other Publications, Page 1: Under "Hand, et al.", change "Tumo-r-associated" to --Tumor-associated--.

Other Publications, Page 2: Under "Kafatos, et al.", change "Nuc. Acids Rec." to --Nucl. Acids Res.--.

UNITED STATES PATENT AND TRADEMARK OFFICE

CERTIFICATE OF CORRECTION

PATENT NO. : 4,957,858 Page 2 of 5

DATED : September 18, 1990

INVENTOR(S) : Chu, et al.

It is certified that error appears in the above-identified patent and that said Letters Patent is hereby corrected as shown below:

Other Publications, Page 2:
Under "Leary, et al.", change "Colorimetic" to --Colorimetric--.

Other Publications, Page 2:
Under "Matthews, et al.", change "Detction" to --Detection--.

Other Publications, Page 2:
Under "Uhlenbeck, et al.", change "Oligoribunucleotides" to --Oligoribonucleotides--.

Other Publications, Page 2:
"Eoyang et al." change volume number from "3" to --2--.

Column 3, Line 58: Change "enzyae-" to --enzyme---.

Column 12, Line 9: Change "is" [first occurrence] to --it--.

Column 12, Line 11: Change "B-elimination" to --β-elimination--.

Column 13, Line 36: Change "$-O(-PO_2)NH(CH_2)_aSS(CH_2)_bNH(PO_2)O-$" to --$-O(-PO_2)NH(CH_2)_aSS(CH_2)_bNH(PO_2)O-$--.

UNITED STATES PATENT AND TRADEMARK OFFICE
CERTIFICATE OF CORRECTION

PATENT NO. : 4,957,858          Page 3 of 5

DATED : September 18, 1990

INVENTOR(S) : Chu, et al.

It is certified that error appears in the above-identified patent and that said Letters Patent is hereby corrected as shown below:

Column 13, Line 51: Change "includes" to --include--.

Column 15, Line 51: Change "Acis" to --Acids--.

Column 19, Line 52: After "7.5", insert --.-- [period].

Column 20, Line 27: Change "5" to --15--.

Column 20, Line 44: Change "to.20" to --to 20--.

Column 20, Line 46: Change "phosophorylated" to --phosphorylated--.

Column 20, Line 66: Change "[5,-$^{32}$P]" to --[5'-$^{32}$P]--.

Column 25, Lines 64-65: Change "-O-PO$_2$-NH(CH$_2$)$_2$SS(CH$_2$)NH$_2$" to ---O-PO$_2$-NH(CH$_2$)$_2$SS(CH$_2$)$_2$NH$_2$--.

Column 27, Line 44: Change "Westerm blot" to --Western blot--.

Column 29, Lines 60-61: Change "-O(-PO$_2$)NH(CH$_2$)$_2$SS(CH$_2$)$_2$NH(PO$_2$)O-" to ---O(PO$_2$)NH(CH$_2$)$_2$SS(CH$_2$)$_2$NH(PO$_2$)O---.

UNITED STATES PATENT AND TRADEMARK OFFICE
CERTIFICATE OF CORRECTION

PATENT NO. : 4,957,858

DATED : September 18, 1990

INVENTOR(S) : Chu, et al.

It is certified that error appears in the above-identified patent and that said Letters Patent is hereby corrected as shown below:

Column 31, Line 36: Between "(b)" and "or", insert --is--.

Column 32, Lines 43-44: (Claim 13) Change "-O-OP-$_2$-NH-$(CH_2)_p(SS)_q(CH_2)_r$NH-" to ---O-$PO_2$-NH-$(CH_2)_p(SS)_q(CH_2)_r$NH---.

Column 32, Line 66: Change "phosphocamidate" to --phosphoramidate--.

Column 33, Line 4: (Claim 17) After "Claim 16", insert --wherein--.

Column 33, Line 32: (Claim 21) Change "reducing" to --reduction--.

Column 34, Lines 24-25: (Claim 29) Change "-O-PO-$_2$-NH-$(CH_2)_m$-S-" to ---O-$PO_2$-NH-$(CH_2)_m$-S---.

Column 34, Lines 49-50: (Claim 33) Change "-O-$PO_2$-N-H-$(CH_2)_p(SS)_q(CH_{2r}$NH-" to ---O-$PO_2$-NH-$(CH_2)_p(SS)_q(CH_2)_r$NH---.

Column 36, Line 11: (Claim 42) Change "nuclei" to --nucleic--.

UNITED STATES PATENT AND TRADEMARK OFFICE

CERTIFICATE OF CORRECTION

PATENT NO. : 4,957,858
DATED : September 18, 1990
INVENTOR(S) : Chu, et al.

It is certified that error appears in the above-identified patent and that said Letters Patent is hereby corrected as shown below:

Column 36, Line 16: (Claim 43) Change "$-O(-PO_2)NH(CH_2)_y(SS)(CH_2)_zNH(PO_2)O-$" to ---$O(PO_2)NH(CH_2)_y(SS)(CH_2)_zNH(PO_2)O$---.

Signed and Sealed this

Twenty-third Day of June, 1992

*Attest:*

DOUGLAS B. COMER

*Attesting Officer*

*Acting Commissioner of Patents and Trademarks*